United States Patent
Heller

(10) Patent No.: US 10,004,439 B2
(45) Date of Patent: *Jun. 26, 2018

(54) IN VIVO SENSORS HAVING CERIA NANOPARTICLE ELECTRODES

(71) Applicant: Abbott Diabetes Care Inc., Alameda, CA (US)

(72) Inventor: Adam Heller, Austin, TX (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/429,267

(22) PCT Filed: Sep. 20, 2013

(86) PCT No.: PCT/US2013/060994
§ 371 (c)(1),
(2) Date: Mar. 18, 2015

(87) PCT Pub. No.: WO2014/047483
PCT Pub. Date: Mar. 27, 2014

(65) Prior Publication Data
US 2015/0230737 A1    Aug. 20, 2015

Related U.S. Application Data

(60) Provisional application No. 61/704,404, filed on Sep. 21, 2012, provisional application No. 61/704,374, filed on Sep. 21, 2012, provisional application No. 61/711,686, filed on Oct. 9, 2012, provisional application No. 61/730,859, filed on Nov. 28, 2012.

(51) Int. Cl.
*G01N 27/327* (2006.01)
*G01N 27/30* (2006.01)
*A61B 5/1468* (2006.01)
*A61B 5/145* (2006.01)

(52) U.S. Cl.
CPC ........ *A61B 5/1468* (2013.01); *A61B 5/14532* (2013.01); *A61B 5/14546* (2013.01)

(58) Field of Classification Search
CPC ............. G01N 27/301; G01N 27/3278; G01N 27/3272; A61B 5/14532; A61B 5/145; A61B 5/14503; A61B 5/14539; A61B 5/14542; A61B 5/14865; A61B 5/1486; B82Y 30/00
See application file for complete search history.

(56) References Cited

U.S. PATENT DOCUMENTS

| | | | |
|---|---|---|---|
| 4,545,382 A | 10/1985 | Higgins et al. | |
| 4,711,245 A | 12/1987 | Higgins et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,320,725 A | 6/1994 | Gregg et al. | |
| 5,356,786 A | 10/1994 | Heller et al. | |
| 5,509,410 A | 4/1996 | Hill et al. | |
| 5,593,852 A | 1/1997 | Heller et al. | |
| 5,601,435 A | 2/1997 | Quy | |
| 5,628,890 A | 5/1997 | Carter et al. | |
| 5,820,551 A | 10/1998 | Hill et al. | |
| 5,822,715 A | 10/1998 | Worthington et al. | |
| 5,899,855 A | 5/1999 | Brown | |
| 5,918,603 A | 7/1999 | Brown | |
| 6,071,391 A | 6/2000 | Gotoh et al. | |
| 6,121,009 A | 9/2000 | Heller et al. | |
| 6,134,461 A | 10/2000 | Say et al. | |
| 6,143,164 A | 11/2000 | Heller et al. | |
| 6,144,837 A | 11/2000 | Quy | |
| 6,161,095 A | 12/2000 | Brown | |
| 6,175,752 B1 | 1/2001 | Say et al. | |
| 6,270,455 B1 | 8/2001 | Brown | |
| 6,284,478 B1 | 9/2001 | Heller et al. | |
| 6,377,894 B1 | 4/2002 | Deweese et al. | |
| 6,413,489 B1 | 7/2002 | Ying | |
| 6,503,381 B1 | 1/2003 | Gotoh et al. | |
| 6,514,460 B1 | 2/2003 | Fendrock | |
| 6,514,718 B2 | 2/2003 | Heller et al. | |
| 6,540,891 B1 | 4/2003 | Stewart et al. | |
| 6,560,471 B1 | 5/2003 | Heller et al. | |
| 6,579,690 B1 | 6/2003 | Bonnecaze et al. | |
| 6,592,745 B1 | 7/2003 | Feldman et al. | |
| 6,600,997 B2 | 7/2003 | Deweese et al. | |
| 6,605,200 B1 | 8/2003 | Mao et al. | |
| 6,605,201 B1 | 8/2003 | Mao et al. | |

(Continued)

FOREIGN PATENT DOCUMENTS

WO    WO 2012/041507    4/2012

OTHER PUBLICATIONS

Babu et al., Nanotechnology, 2009, 20, 1-5.*

(Continued)

*Primary Examiner* — Gurpreet Kaur
(74) *Attorney, Agent, or Firm* — Meunier Carlin & Curfman LLC

(57) ABSTRACT

Ceria nanoparticle compositions for use as electrode materials for in vivo electrochemical analyte sensors (e.g., glucose sensors) are provided, for example to form a cathode or a reference electrode. The ceria nanoparticle compositions may be combined with a conductive material (e.g., mixed with) to form the cathode or the reference electrode, or the ceria nanoparticle compositions may be deposited over conductive material to form the cathode or the reference electrode. Electrochemical in vivo sensors for monitoring the concentration of an analyte having a reference electrode and/or a cathode that includes a ceria nanoparticle composition, and methods for monitoring an analyte concentration using the electrochemical sensors are also described. Methods of making in vivo electrochemical analyte sensors having a reference electrode and/or a cathode that includes a ceria nanoparticle composition are also provided.

25 Claims, 15 Drawing Sheets

(56) References Cited

U.S. PATENT DOCUMENTS

| | | |
|---|---|---|
| 6,616,819 B1 | 9/2003 | Liamos et al. |
| 6,654,625 B1 | 11/2003 | Say et al. |
| 6,676,816 B2 | 1/2004 | Mao et al. |
| 6,730,200 B1 | 5/2004 | Stewart et al. |
| 6,736,957 B1 | 5/2004 | Forrow et al. |
| 6,746,582 B2 | 6/2004 | Heller et al. |
| 6,764,581 B1 | 7/2004 | Forrow et al. |
| 6,881,551 B2 | 4/2005 | Heller et al. |
| 6,893,545 B2 | 5/2005 | Gotoh et al. |
| 6,932,894 B2 | 8/2005 | Mao et al. |
| 7,090,756 B2 | 8/2006 | Mao et al. |
| 7,167,818 B2 | 1/2007 | Brown |
| 7,299,082 B2 | 11/2007 | Feldman et al. |
| 7,501,053 B2 | 3/2009 | Karinka et al. |
| 7,811,231 B2 | 10/2010 | Jin et al. |
| 7,822,557 B2 | 10/2010 | Chen et al. |
| 8,106,780 B2 | 1/2012 | Goodnow et al. |
| 8,172,997 B2 | 5/2012 | Seal et al. |
| 2002/0098119 A1 | 7/2002 | Goodman |
| 2005/0051440 A1* | 3/2005 | Simpson ............ A61B 5/14532 205/778 |
| 2006/0025662 A1 | 2/2006 | Buse et al. |
| 2006/0091006 A1 | 5/2006 | Wang et al. |
| 2006/0253012 A1 | 11/2006 | Petisce |
| 2007/0042377 A1 | 2/2007 | Gao et al. |
| 2007/0068807 A1 | 3/2007 | Feldman et al. |
| 2007/0095661 A1 | 5/2007 | Wang et al. |
| 2007/0108048 A1 | 5/2007 | Wang et al. |
| 2007/0199818 A1 | 8/2007 | Petyt et al. |
| 2008/0066305 A1 | 3/2008 | Wang et al. |
| 2008/0102441 A1 | 5/2008 | Chen et al. |
| 2008/0148873 A1 | 6/2008 | Wang |
| 2008/0177164 A1 | 7/2008 | Heller et al. |
| 2008/0179187 A1 | 7/2008 | Ouyang et al. |
| 2008/0267823 A1 | 10/2008 | Wang et al. |
| 2009/0071848 A1 | 3/2009 | Seal et al. |
| 2009/0095625 A1 | 4/2009 | Forrow |
| 2010/0198034 A1 | 8/2010 | Thomas et al. |
| 2010/0213057 A1 | 8/2010 | Feldman et al. |
| 2010/0324392 A1 | 12/2010 | Yee et al. |
| 2010/0326842 A1 | 12/2010 | Mazza et al. |
| 2011/0003084 A1 | 1/2011 | Berghaus et al. |
| 2011/0048275 A1 | 3/2011 | Fletcher |
| 2011/0120865 A1 | 5/2011 | Bommakanti et al. |
| 2011/0124993 A1 | 5/2011 | Bommakanti et al. |
| 2011/0124994 A1 | 5/2011 | Bommakanti et al. |
| 2011/0126188 A1 | 5/2011 | Bernstein et al. |
| 2011/0210726 A1* | 9/2011 | Cui ..................... C12Q 1/004 324/252 |
| 2011/0213225 A1 | 9/2011 | Bernstein et al. |
| 2011/0256024 A1 | 10/2011 | Cole et al. |
| 2011/0257495 A1 | 10/2011 | Hoss et al. |
| 2012/0157801 A1 | 6/2012 | Hoss et al. |
| 2012/0245447 A1 | 9/2012 | Karan et al. |
| 2012/0257801 A1 | 10/2012 | Wada |
| 2012/0315659 A1 | 12/2012 | Andreescu et al. |
| 2012/0323098 A1 | 12/2012 | Moein et al. |
| 2013/0045416 A1 | 2/2013 | Seferos et al. |
| 2014/0042038 A1 | 2/2014 | Bhansali |

OTHER PUBLICATIONS

Kosacki et al., Solid State Ion, 149, 99.*
Feldman et al. (2003) "A continuous glucose sensor based on Wired Enzyme™ technology—Results from a 3-day trial in patients with type 1 diabetes." Diabetes technology & therapeutics 5.5:769-779.
Ohara et al. (1993) "Glucose electrodes based on cross-linked bis(2,2'-bipyridine)chloroosmium(+/2+) complexed poly(1-vinylimidazole) films" Anal. Chem. 65(23):3512-3517.

* cited by examiner

C

D

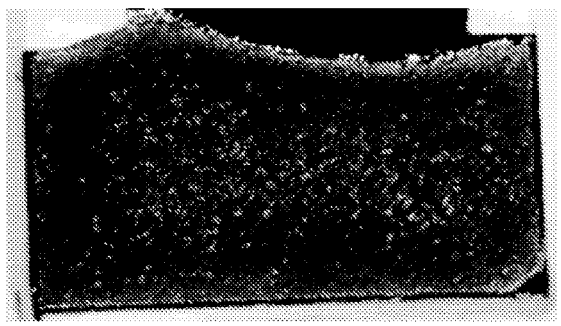
A
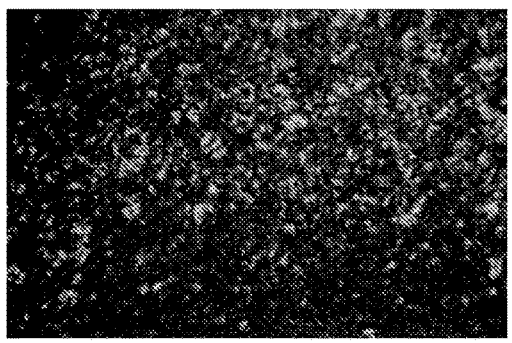
B
FIG. 19
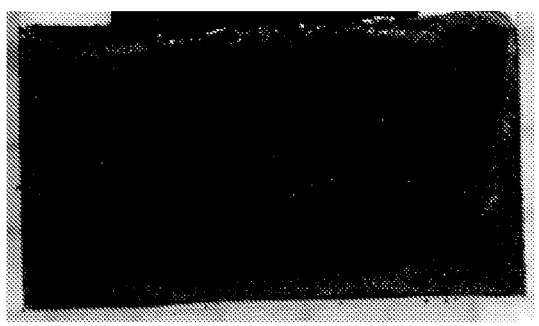
C
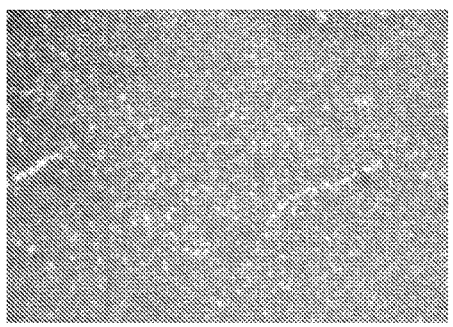
D

IN VIVO SENSORS HAVING CERIA NANOPARTICLE ELECTRODES

CROSS-REFERENCE TO RELATED APPLICATIONS

This application claims priority based on U.S. Provisional Application No. 61/704,404, filed Sep. 21, 2012, U.S. Provisional Application No. 61/704,374, filed Sep. 21, 2012, U.S. Provisional Application No. 61/711,686, filed Oct. 9, 2012, and U.S. Provisional Application No. 61/730,859, filed Nov. 28, 2012, the disclosures of which are incorporated by reference herein in their entirety.

INTRODUCTION

In the management and diagnosis of diabetes, it is desirable or necessary to regularly monitor the concentration of particular constituents in a fluid. A number of systems are available that analyze the constituents of bodily fluids such as blood, urine and saliva. Examples of such systems conveniently monitor the level of particular medically significant fluid constituents, such as, for example, cholesterol, ketones, vitamins, proteins, and various metabolites or blood sugars, such as glucose. Diagnosis and management of patients suffering from diabetes mellitus, a disorder of the pancreas where insufficient production of insulin prevents normal regulation of blood sugar levels, requires carefully monitoring of blood glucose levels on a daily basis.

Accordingly, it would be desirable to have systems that monitor the concentration of particular constituents in a fluid, such as glucose.

SUMMARY

Ceria nanoparticle compositions for use as electrode materials for in vivo electrochemical analyte sensors (e.g., glucose sensors) are provided, for example to form a cathode or a reference electrode. The ceria nanoparticle compositions may be combined with a conductive material (e.g., mixed with) to form the cathode or the reference electrode, or the ceria nanoparticle compositions may be deposited over conductive material to form the cathode or the reference electrode. Electrochemical in vivo sensors for monitoring the concentration of an analyte having a reference electrode and/or a cathode that includes a ceria nanoparticle composition, and methods for monitoring an analyte concentration using the electrochemical sensors are also described. Methods of making in vivo electrochemical analyte sensors having a reference electrode and/or a cathode that includes a ceria nanoparticle composition are also provided.

BRIEF DESCRIPTION OF THE FIGURES

FIGS. 19A-D shows a series of micrographs of dried ceria-carbon paste coated on conventional printed carbon electrodes.

DETAILED DESCRIPTION

Figure 1:
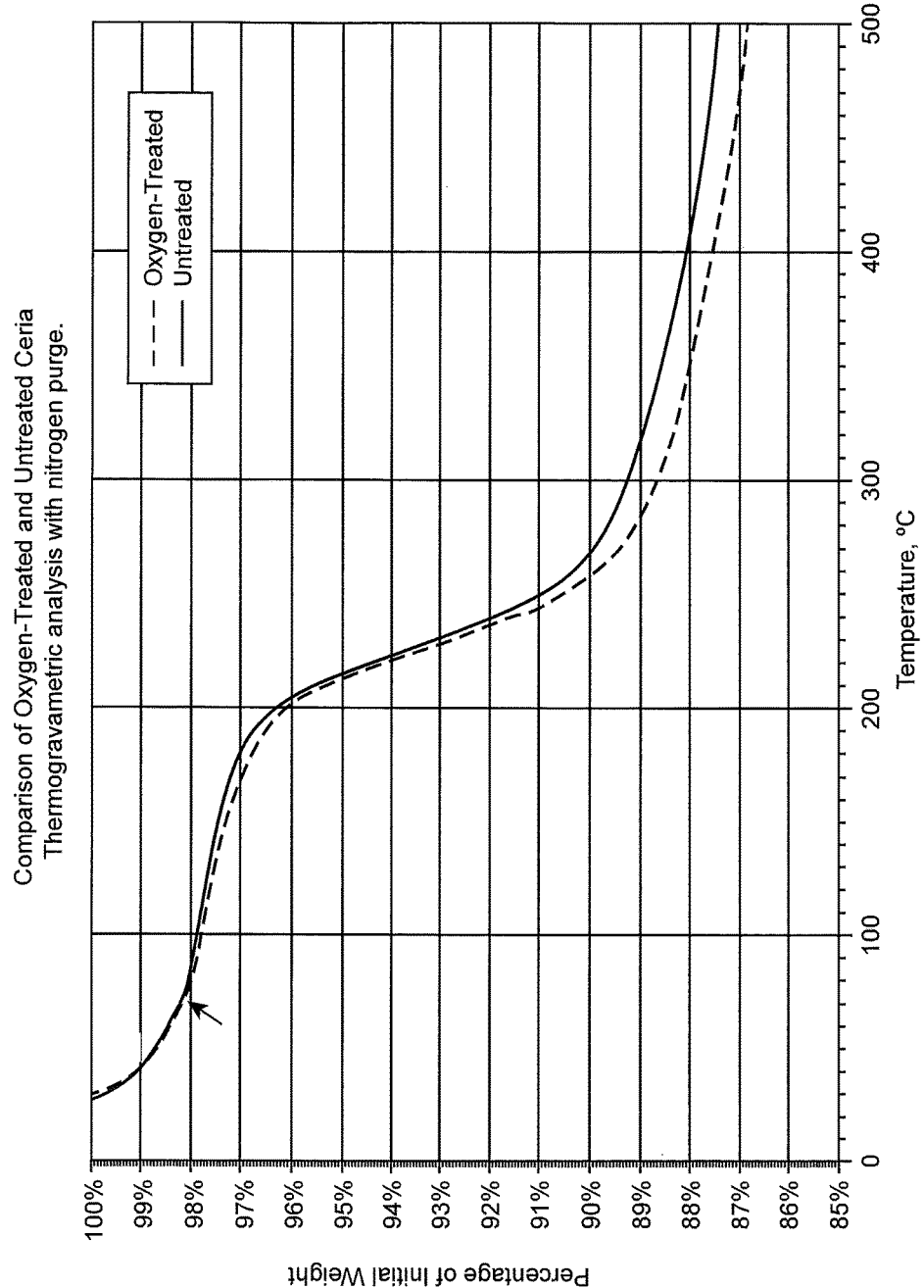
FIG. 1 shows an example of thermogravimetric analyses of oxygenated and non-oxygenated ceria nanoparticles.

Electrochemical systems for continuous glucose monitoring may include an in vivo sensor having at least one anode, at least one cathode and typically a reference electrode that are positioned in fluidic communication with the fluids of the skin e.g. those of the dermis or the subcutis. In-vivo electrochemical sensors detect analytes via electrical signals (e.g., current in amperometric biosensors) by monitoring an electron flux resulting of biochemical reactions of bioanalytes. In certain in-vivo electrochemical sensors, the analyte of interest is oxidized at the anode held at a defined potential versus the potential of the reference electrode, and oxygen or water or another oxidant is reduced at the cathode. Described herein are ceria nanoparticle compositions that are suitable for use as a redox couple at the cathode or the reference electrode. Use of a redox couple at the reference electrode or cathode that is less soluble in biological fluids and/or is less reactive with biological molecules than the often used silver chloride is particularly advantageous since it avoids loss of activity and/or diffusion of the redox couple while the sensor is positioned in vivo.

Before the ceria nanoparticle compositions, electrochemical sensors and methods of the present disclosure are described in greater detail, it is to be understood that the sensors and methods are not limited to particular embodiments described, as such may, of course, vary. It is also to be understood that the terminology used herein is for the purpose of describing particular embodiments only, and is not intended to be limiting, since the scope of the sensors and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the sensors and methods. The upper and lower limits of these smaller ranges may independently be included in the smaller ranges and are also encompassed within the sensors and methods, subject to any specifically excluded limit in the stated range. Where the stated range includes one or both of the limits, ranges excluding either or both of those included limits are also included in the sensors and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods and materials similar or equivalent to those described herein can also be used in the practice or testing of the sensors and methods, representative illustrative sensors, methods and materials are now described.

All publications and patents cited in this specification are herein incorporated by reference as if each individual publication or patent were specifically and individually indicated to be incorporated by reference and are incorporated herein by reference to disclose and describe the sensors, methods and/or materials in connection with which the publications are cited. The citation of any publication is for its disclosure prior to the filing date and should not be construed as an admission that the present sensors and methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Certain features of the electrodes, sensors and methods, which are, for clarity, described in the context of separate embodiments, may also be provided in combination in a single embodiment. Conversely, various features of the sensors and methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present sensors and methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present sensors and methods. Any recited method can be carried out in the order of events recited or in any other order which is logically possible.

Ceria Nanoparticle Compositions

As summarized above, electrodes comprising compositions having ceria nanoparticles and electrochemical sensors that use ceria nanoparticle compositions are disclosed. The ceria nanoparticle compositions may be employed in an electrochemical analyte sensor such as on a surface of a conductive material (e.g., layered over at least a portion of a conductive material) or combined with a conductive material (e.g., mixed with a conductive material) to form a cathode or reference electrode, or both a cathode and a reference electrode, of the electrochemical analyte sensor.

In embodiments of the present disclosure, ceria nanoparticle compositions include ceria nanoparticles. The term "ceria" is used in its conventional sense to refer any oxide of cerium, such as solid cerium oxide and can have oxidation states of +3 (cerium III) and +4 (cerium IV) in any ratio. Ceria nanoparticles are described by the formula $CeO_{2-x}$, where x typically ranges from 0 to 0.5 depending on the number of cerium atoms in the crystalline lattice have a valence of +3 and cerium atoms having a valence of +4. Accordingly, embodiments according to certain aspects include compositions having ceria nanoparticles of the formula $CeO_{2-x}$ where x is between 0.01 and 0.1, or is 0.1 or greater, such as 0.15 or greater, such as 0.2 or greater, such as 0.25 or greater, such as 0.30 or greater, such as 0.35 or greater, such as 0.4 or greater, such as 0.45 or greater, such as 0.49 or greater and including ceria nanoparticles of the formula $CeO_{2-x}$ where x is 0.5. In certain embodiments, cerium atoms in ceria nanoparticles according to the present disclosure have a valence of not less than +3 (i.e., in ceria nanoparticles of the formula $Ce_2O_3$) and not more than +4 (i.e., in ceria nanoparticles of the formula $CeO_2$).

Compositions of interest may include one or more forms of ceria nanoparticles. For example, a given composition may include ceria nanoparticles of the formula $CeO_{2-x}$ where x varies from 0.01 to 0.5, for example from 0.1 to 0.5. In other instances, depending on the source of ceria, storage conditions, and the desired electrode (e.g., cathode or reference electrode) properties, compositions of interest may include particular forms of ceria nanoparticles. In some instances ceria nanoparticles having a value of x of 0.2 or greater may be 50% or greater of the total weight of ceria nanoparticles in the composition, such as 60% or greater, such as 75% or greater, such as 90% or greater, such as 95% or greater and including 99% or greater of the total weight of ceria nanoparticles in the composition. In other embodiments, ceria nanoparticles having a value of x of 0.3 or greater may be 50% by weight or greater of the total weight of ceria nanoparticles in the composition, such as 60% by weight or greater, such as 75% by weight or greater, such as 90% by weight or greater, such as 95% by weight or greater and including 99% by weight or greater. In yet other instances, ceria nanoparticles having a value of x of 0.5 may be 50% by weight or greater of the total weight of ceria nanoparticles in the composition, such as 60% by weight or greater, such as 75% by weight or greater, such as 90% by weight or greater, such as 95% by weight or greater and including 99% by weight or greater.

As such, depending on the type of electrode (e.g., reference electrode or cathode) employing the ceria nanoparticle compositions described herein, the valence state of the ceria nanoparticles bulk and/or of their surface may vary. In certain embodiments, ceria nanoparticles and/or ceria nanoparticle surfaces in the ceria nanoparticle composition are electroreducible, for example in certain cathode embodiments. In other embodiments, ceria nanoparticles and/or ceria nanoparticle surfaces in the ceria nanoparticle composition are both electroreducible and electrooxidizable, i.e. of mixed valence, for example in certain reference electrode embodiments. The term "electroreducible" is used herein in its conventional sense to refer to a state in which the $Ce^{4+}$ and/or bound oxygen in the ceria nanoparticles or at their surface can act as an oxidant (i.e., accept one or more electrons). For example, in embodiments in which a ceria nanoparticle composition is used to form a cathode, the ceria nanoparticles may be at least mostly electroreducible. The term "electrooxidizable" is used herein in its conventional sense to refer to a state in which the ceria nanoparticles can act as a reductant (i.e., donate one or more electrons). In reference electrodes embodiments, ceria nanoparticles in the ceria nanoparticle composition may be both electroreducible and electrooxidizable (i.e., of mixed valence, can accept or donate electrons). For example, in embodiments in which a ceria nanoparticle composition is used to form a reference electrode, the ceria nanoparticles, and/or their surfaces, may be both electroreducible and electrooxidizable.

Ceria nanoparticles according to the present disclosure may include lattice defect sites, often at or near the surface of the nanoparticles, which allow oxygen absorption by the ceria nanoparticles. By "lattice defect" is meant irregularities in the three-dimensional structure which gives rise to vacancies within the crystalline lattice so that ceria nanoparticles are capable of storing oxygen. Lattice defects are typically at or near the surface of the nanocrystallites, and may also include, but are not limited to, oxygen anion vacancy defects, self-interstitials, interstitial impurity atoms and edge dislocations.

In some embodiments, compositions may include ceria nanoparticles having oxygen anion vacancy defects. By "oxygen anion vacancy defect" is meant a vacant site of the crystalline lattice where an $O^{2-}$ anion would occupy in a $CeO_2$ lattice. The amount of oxygen anion vacancy defects in ceria nanoparticles of certain compositions may vary depending on the desired oxygen loading and may be 1% or more of oxygen sites in the crystalline structure, such as 2% or more, such as 3% or more, such as 5% or more, such as 10% or more, such as 15% or more and including 20% or more of the oxygen sites in the crystalline structure may be vacant to facilitate the storage of oxygen.

In other embodiments, ceria nanoparticle compositions of interest include ceria nanoparticles having lattice defect sites, such as for example, by doping the ceria nanoparticle with one or more dopants. For example, compositions may include ceria nanoparticles doped with one or more of lanthanum, gadolinium, samarium, ytterbium, copper, manganese, zinc, cobalt, praseodymium, calcium, zirconium, aluminum, terbium, combinations thereof, among other dopants. Ceria nanoparticles may be doped with an amount of dopant to produce ceria nanoparticles having 1 mole percent or more dopant, such as 2 mole percent or more, such as 3 mole percent or more, such as 5 mole percent or more, such as 10 mole percent or more, such as 15 mole percent or more, such as 20 mole percent or more and including 25 mole percent or more of the dopant. Where ceria nanoparticles include two or more dopants, the amount of each dopant may vary depending on the oxygen loading desired. For example, each dopant may be 1 mole percent or more, such as 2 mole percent or more, such as 3 mole percent or more, such as 5 mole percent or more, such as 8 mole percent or more, such as 10 mole percent or more, and including 12 mole percent or more.

The amount of absorbed oxygen loaded into the nanoparticles may vary depending on the particle size, increasing when the particles are smaller and on the number of lattice vacancies as well as other properties of the ceria nanoparticles. Since $Ce^{3+}$ sites within or at the surface of the crystalline lattice of ceria nanoparticles are required for the absorption of oxygen, partial reduction of $CeO_2$ to $CeO_{2-x}$ increases the amount of absorbed oxygen. Absorbed oxygen can be, for example, molecular oxygen (i.e., $O_2$), bound superoxide radical anion (i.e., $.O_2^-$) or superoxide radical (.OOH). At least part of the ceria nanoparticle compositions is regenerated by reaction with dissolved oxygen at atmospheric pressure and at a temperature between about 25° C. and 40° C. The amount of absorbed oxygen loaded into the subject ceria nanoparticles may be 1 percent by weight or more, such as 2 percent by weight or more, such as 3 percent by weight or more, such as 5 percent by weight or more, such as 10 percent by weight or more, such as 15 percent by weight or more and including a molecular oxygen loading of 25 percent by weight or more.

The sizes of ceria nanoparticles in a given composition may vary and are therefore polydisperse, having diameters ranging from 1 nm to 100 nm, such as 2 nm to 90 nm, such as 5 nm to 75 nm, such as 10 nm to 50 nm, such as 15 nm to 40 nm, including 10 nm to 20 nm. For example, ceria nanoparticles may have diameters ranging from 2 nm to 10 nm. Alternatively, ceria nanoparticles may have diameters ranging from 10 nm to 20 nm or from 20 nm to 50 nm.

In certain embodiments, compositions include ceria nanoparticles which have a narrow range of sizes such that the ceria nanoparticles in a given composition are all similar in size, and deviation from the average particle size is no greater than 5 nm, such as no greater than 4 nm, such as no greater than 3 nm. For example, a given composition according to certain embodiments may include ceria nanoparticles which have sizes ranging from 1 nm to 5 nm, from 5 nm to 10 nm, from 10 nm to 15 nm, from 15 nm to 20 nm, including from 20 nm to 25 nm. In other embodiments, compositions may include ceria nanoparticles which have sizes ranging from 1 nm to 2.5 nm, from 2.5 nm to 5 nm, from 5 nm to 7.5 nm, from 7.5 nm to 10 nm, from 10 nm to 12.5 nm and including from 12.5 nm to 15 nm. In certain embodiments, compositions include ceria nanoparticles which all have the same size (i.e., are monodisperse or uniform) as well as having varying sizes (i.e., are polydisperse).

In some embodiments, compositions are formed of colloidal solutions of ceria nanoparticles. The term "colloidal ceria nanoparticles" is used in its conventional sense to refer to solid ceria nanoparticles dispersed though a liquid medium (e.g., water) and include but is not limited to colloidal ceria emulsions or colloidal ceria dispersions. The amount of ceria nanoparticles in the colloidal composition ranges from 5% by weight to 50% by weight, such as 10% by weight to 45% by weight, such as 15% by weight to 40% by weight, such as 20% by weight to 35% by weight and including 25% by weight to 30% by weight.

The total mass of ceria nanoparticles within a given composition applied within a reference electrode ranges typically from 0.1 mg to 100 mg, such as 0.1 mg to 10 mg, whereas the mass applied within a cathode typically ranges from 5 to 1000 mg, such as 10 mg to 750 mg, such as 25 mg to 500 mg, such as 50 to 250 mg, such as 75 mg to 150 mg and including 100 mg of ceria nanoparticles. As such, the weight percentage of ceria nanoparticles in compositions of interest may be 1% by weight or more, such as 2% by weight or more, such as 5% by weight or more, such as 10% by weight or more, such as 15% by weight or more, such as 20% by weight or more, such as 25% by weight or more, such as 30% by weight or more, such as 35% by weight or more and including 50% by weight or more ceria nanoparticles. In some embodiments, the weight percentage of ceria nanoparticles ranges between 1% by weight and 95% by weight, such as between 10% by weight and 80% by weight, including between 20% by weight and 70% by weight.

Where the subject compositions include colloidal ceria nanoparticles, the total dry mass of colloidal ceria nanoparticles in the composition applied within a reference electrode may range from 0.1 mg to 100 mg, such as 0.1 mg to 10 mg, whereas the mass applied within a cathode may range from 5 to 1000 mg such as 10 mg to 750 mg, such as 25 mg to 500 mg, such as 50 to 250 mg, such as 75 mg to 150 mg and including 100 mg of ceria nanoparticles. For example, where the colloid is 50% by weight ceria nanoparticles, compositions may include from 10 mg to 2000 mg of the colloidal ceria nanoparticles, such as 20 mg to 1500 mg, such as 50 mg to 1000 mg, such as 100 mg to 500 mg, such as 150 mg to 300 mg and including 200 mg colloidal ceria nanoparticles.

Aspects of the disclosure include in vivo analyte electrochemical sensors that have compositions having ceria nanoparticles, such as for example that have a ceria nanoparticle composition-cathode and/or ceria nanoparticle composition-reference electrode. In some embodiments, ceria nanoparticle compositions are operably associated with one or more conductive materials to form an in vivo analyte sensor, for example may be layered with or mixed with a conductive material(s). A conductive material used may be any suitable electrical conductor, including but not limited to, gold, carbon, platinum or other platinum group metal, platinum-carbon, doped-tin oxide, indium tin oxide, ruthenium, ruthenium dioxide, palladium, silver, copper, nickel, rhodium, cobalt, zinc, titanium as well as conductive polymers, described in greater detail below, and combinations thereof. In some embodiments of electrochemical sensors, the conductive material is conductive carbon. Conductive carbon, such as a carbon black, may be formed of branched chain-forming particles having diameters smaller than 50 nm, such as 20 nm, such as 10 nm, such as 5 nm and including a diameter smaller than 2 nm. The carbon can be treated by exposure to plasma in the presence of oxygen or air at reduced pressure (e.g., 0.2 to 10 Torr) to improve wetting or to allow suspension of the carbon particles in water.

The amount of conductive material mixed with the compositions of interest may vary, depending on the size of the electrode, the amount of ceria nanoparticles and desired application of the electrode. For example, the amount of conductive material mixed with the composition to form a reference electrode may range from 0.1 mg to 100 mg, such as 0.1 mg to 10 mg, whereas the amount of conductive material mixed with the composition to form within a cathode may range from 5 to 1000 mg, such as 10 mg to 750 mg, such as 25 mg to 500 mg, such as 50 to 250 mg, such as 75 mg to 150 mg and including 100 mg of conductive material. As such, the weight percent of conductive material in the conductive ceria compositions of interest may be 1% by weight or more, such as 2% by weight or more, such as 5% by weight or more, such as 10% by weight or more, such as 15% by weight or more, such as 20% by weight or more, such as 25% by weight or more, such as 30% by weight or more, such as 35% by weight or more, such as 50% by weight or more and including 60% by weight or more conductive material.

The weight ratio of ceria nanoparticles to conductive material in a composition may range from 1:1 and 1:2.5; 1:2.5 and 1:5; 1:5 and 1:10; 1:10 and 1:25; 1:25 and 1:50; 1:50 and 1:100 or a range thereof. For example, the weight ratio of ceria nanoparticles to conductive material in ceria nanoparticle compositions may range between 1:1 and 1:10; 1:5 and 1:25; 1:10 and 1:50; or 1:25 and 1:100. Alternatively, the weight ratio of conductive material to ceria nanoparticles in the composition may range from between 1:1 and 1:2.5; 1:2.5 and 1:5; 1:5 and 1:10; 1:10 and 1:25; 1:25 and 1:50; 1:50 and 1:100, or a range thereof. For example, the weight ratio of conductive material to ceria nanoparticles in compositions of interest may range between 1:1 and 1:10; 1:5 and 1:25; 1:10 and 1:50; or 1:25 and 1:100.

The wet, but not the dried compositions of which electrodes are made may further include one or more inorganic or organic acids. The inorganic acid can be for example acetic acid, nitric acid or hydrochloric acid. The organic acid may be any suitable organic acid, such as acetic acid or a halogenated (e.g., fluorinated) organic acid, including but not limited to trifluoroacetic acid (TFA), perfluorooctanoic acid (PFOA), heptafluorobutyric acid, trifluorobutyric acid, trifluoropropionic acid, combinations thereof, among other organic acids. The concentration of the inorganic or organic acid in ceria nanoparticle compositions may vary, depending on the amount of conductive material and ceria nanoparticles. For example, the concentration of organic acid may range from 0.01 w/v % to 1 w/v %, such as 0.05 w/v % to 1 w/v %, such as 0.1 w/v % to 0.9 w/v %, such as 0.15 w/v % to 0.75 w/v %, such as 0.2 w/v % to 0.6 w/v %, including 0.1 w/v % to 0.5 w/v %.

The weight ratio of inorganic or organic acid to ceria nanoparticles in compositions of interest may range between 1:1 and 1:10; 1:5 and 1:25; 1:10 and 1:50; or 1:25 and 1:100; 1:50 and 1:500; or 1:100 and 1:1000.

Ceria nanoparticle compositions may further include one or more binders. The binder may be cured to further bind the conductive material and ceria nanoparticles together in the composition. In certain instances, curing the binder increases the conductivity of the composition. By "increases the conductivity" is meant that a composition where the binder is cured has a conductivity which is greater than if the binder were not present and/or uncured. Increased conductivity may be 10% greater than a composition having the same binder but is left uncured, such as 25% greater, such as 50% greater, such as 75% greater and including a conductivity which 100% greater than the conductivity of a composition having the same binder but is left uncured.

Binder compositions may include one or more organic polymers. For example, the polymer may be a heterocyclic-nitrogen containing polymer or a water swellable polymer. Polymers may also be crosslinked, such as with two or more glycidyl moieties. Suitable polymers may include polymers which are water soluble prior to crosslinking and may swell in the presence of water, but do not substantially dissolve in water after crosslinking or curing. The subject polymers may include, for example, primary, secondary, tertiary or quaternary amine functions, aliphatic amine groups, (such as for example, polyethyleneimine or polyallylamine) or heterocyclic nitrogen-containing groups (e.g., poly-N-vinylimidazole, poly-2 or 4-vinylpyridine or partially N-alkylated ammonium salts of poly-2 or 4-vinylpyridine). Organic polymers of the present disclosure may be conductive polymers, such as polycationic polymers, polyanionic polymers (e.g., polymers having sulfonic acid and/or carboxylic acid or other ionizable acidic moieties) or zwitterionic polymers (i.e., polymers having both anionic and cationic moieties). Organic polymers may further include a crosslinking agent, such as for example a glycidyl crosslinker (e.g., polyethyleneglycol diglycidyl ether, PEGDGE). The polymers may also include polymers that are not ionic and do not swell in water, such as polyvinylidene fluoride, known as PVDF.

The amount of organic polymer in ceria nanoparticle compositions of the present disclosure may vary, depending on the size of the electrode, the amount of ceria nanoparticles and desired properties of the electrode. For example, the amount of organic polymer in a reference electrode may range from 0.1 mg to 100 mg, such as 0.1 mg to 10 mg, while in a cathode it may range from 5 to 1000 mg, such as 10 mg to 750 mg, such as 25 mg to 500 mg, such as 50 to 250 mg, such as 75 mg to 150 mg and including 100 mg of organic polymer. As such, the weight percentage of organic polymer in compositions may be 1% by weight or more, such as 2% by weight or more, such as 5% by weight or more, such as 10% by weight or more, such as 15% by weight or more, such as 20% by weight or more, such as 25% by weight or more, such as 30% by weight or more, such as 35% by weight or more and including 50% by weight or more conductive material. In some embodiments, the weight percentage of the organic polymer ranges between 1% to 50% by weight, such as 1% to 5% by weight, such as 5% to 10% by weight, such as 10% to 20% by weight, such as 20% to 30% by weight, such as 30% to 40% by weight, and including 40% to 50% by weight.

The weight ratio of ceria nanoparticles to organic polymer in the composition ranges from 1:1 and 1:2.5; 1:2.5 and 1:5; 1:5 and 1:10; or a range thereof. For example, the weight ratio of ceria nanoparticles to organic polymer in compositions may range between 1:1 and 1:2.5; 1:2.5 and 1:5; 1:5 and 1:10 or a range thereof.

Suitable binders may further include, but are not limited to, polyurethane resins, cellulose derivatives, elastomers, and highly fluorinated polymers. Examples of elastomers include silicones, polymeric dienes, and acrylonitrile-butadiene-styrene (ABS) resins. These binders may be cured using, for example, heat or light, including ultraviolet (UV) light. The appropriate curing method typically depends on the particular binder which is used.

The amount of binder in the composition varies depending on the amount of ceria nanoparticles and conductive material in a given composition. The weight percent of binders in subject compositions may be 1% by weight or more, such as 2% by weight or more, such as 5% by weight or more, such as 10% by weight or more, such as 15% by weight or more, such as 20% by weight or more and including 25% by weight or more binder. As such, the total amount of binder in a given composition may range in reference electrodes from 0.1 mg to 100 mg and in cathodes from 5 to 1000 mg, such as 10 mg to 750 mg, such as 25 mg to 500 mg, such as 50 to 250 mg, such as 75 mg to 150 mg and including 100 mg.

The weight ratio of binder to ceria nanoparticles in the composition may range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the weight ratio of binder to ceria nanoparticles in the composition may range between 1:1 and 1:10; 1:5 and 1:25; 1:10 and 1:50; or 1:25 and 1:100; 1:50 and 1:500; or 1:100 and 1:1000.

In certain embodiments, compositions may include one or more polyanionic, or polycationic or zwitterionic polymers. The polyanionic polymer may be any suitable negatively charged polymer, including but not limited to polystyrenesulfonic acid, polyacrylic acid or a fluorinated polysulfonic acid like Nafion. The polycationic polymer may be any suitable positively charged polymer, including but not limited to polyallylamine, chitosan, poly-2-vinylpyridine, poly-2-vinyl-N-methylpyridinium hydroxide, poly-4-vinylpyridine, poly-4-vinyl-N-methylpyridinium hydroxide, poly-2-vinylpyridine-N-oxide, poly-2-vinylpyridine-N-hydroxide, poly-N-vinylimidazole and poly-4-vinylpyrdine co-polyethylene oxide, un-crosslinked and di-, tri- or poly-epoxide cross-linked polyamines, cationic polyacrylates and polymethacrylates or combinations thereof. Zwitterionic polymers can be, for example, poly(2-vinyl pyridine sulfopropyl betaine) or poly(4-vinyl pyridine sulfopropyl betaine).

The amount of cationic polymer or zwitterionic in the composition varies depending on the amount of ceria nanoparticles and conductive material in a given composition. The weight percent of cationic polymer in subject compositions may be 1% by weight or more, such as 2% by weight or more, such as 5% by weight or more, such as 10% by weight or more, such as 15% by weight or more, such as 20% by weight or more and including 25% by weight or more cationic or zwitterionic polymer. As such, the total amount of cationic or zwitterionic polymer in a given composition may range in reference electrodes from 0.1 mg to 100 mg and in cathodes from 5 to 1000 mg, such as 10 mg to 750 mg, such as 25 mg to 500 mg, such as 50 to 250 mg, such as 75 mg to 150 mg and including 100 mg.

The weight ratio of ceria nanoparticles to cationic or zwitterionic polymer in the composition ranges from 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof.

For example, the weight ratio of ceria nanoparticles to cationic or zwitterionic polymer may range between 1:1 and 1:10; 1:5 and 1:25; 1:10 and 1:50; 1:25 and 1:100; 1:50 and 1:500; or 1:100 and 1:1000. Alternatively, the weight ratio of cationic or zwitterionic polymer to ceria nanoparticles in the composition ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the weight ratio of cationic or zwitterionic polymer to ceria nanoparticles in the composition may range between 1:1 and 1:10; 1:5 and 1:25; 1:10 and 1:50; or 1:25 and 1:100; 1:50 and 1:500; or 1:100 and 1:1000.

Although the above compositions have been specifically described with ceria nanoparticles, the subject compositions may alternatively include nanoparticles of any lanthanide oxide or actinide oxide or a combination thereof. The term "lanthanide" is used in its conventional sense to refer to the fifteen chemical elements having atomic numbers from 57 to 71. As such, lanthanide oxides of the present disclosure include mixed valence oxides of the elements cerium, praseodymium, samarium, terbium, dysprosium, holmium and erbium. Similarly, the term "actinide" is used in its conventional sense to refer to the less radioactive and long lived mixed valence oxides of thorium and uranium.

Ceria Nanoparticle Cathodes

Aspects of the present disclosure also include cathodes having one or more of the subject ceria nanoparticle compositions. In certain embodiments, an amount of ceria nanoparticle composition is deposited on surface of a conductive material (e.g., layered over the conductive material) to form a cathode. The conductive material may be deposited over an inert non-conducting substrate or the conductive material may itself provide the structural support of an electrode that can be, for example, planar or have, for example, the form of a needle or a wire. In other embodiments, an amount of ceria nanoparticle composition is combined with a conductive material to form a cathode, for example mixed with the conductive material to provide a conductive ceria nanoparticle composition. The conductive ceria nanoparticle composition may alternatively be formed or shaped to provide the structural support to act as an electrode while in use, such as, for example, a needle or a wire. Both a conductive layer and a conductive ceria nanoparticle composition may be used in a single electrode or plurality of electrodes of a single sensor, in certain instances.

The cathode can have a variety of forms and can be made from a variety of materials. For example, the cathode can be planar, formed for example as a plate, or have the form of a mesh, tube, wire, or have another shape. A cathode may be planar as well as non-planar, and an exterior surface, an interior surface, or a combination of exterior and interior surfaces, may be designed to be fluidic contact with the biological fluid when the cathode is positioned in vivo.

The ceria nanoparticle composition may be applied to a surface of a substrate by a variety of methods, including, for example hot or cold spraying drop casting, spin casting, sputtering, doctor blading printed on a flat surface or in an embossed or otherwise recessed surface, transferred from a separate carrier or liner, etched, or molded physical vapor deposition, plasma deposition, chemical vapor deposition and printing among other deposition methods. Suitable methods of printing include screen-printing, piezoelectric printing, ink jet printing, laser printing, photolithography, painting, gravure roll printing, transfer printing, and other known printing methods.

The cathode substrate may be any suitable size, as desired, having a length which ranges from 0.1 mm to 5.0 mm, such as from 0.5 mm to 4.5 mm, such as from 1.0 mm to 4.0 mm, such as from 1.5 mm to 3.0 mm and including 2.5 mm and a width which ranges from 0.1 mm to 5.0 mm, such as from 0.5 mm to 4.5 mm, such as from 1.0 mm to 4.0 mm, such as from 1.5 mm to 3.0 mm and including 2.5 mm. A cathode width may be uniform along its entire length or may vary. Shorter or longer lengths and narrower or wider widths may also suitable. The geometric area of the cathode substrate may range from 0.01 $mm^2$ to 25.0 $mm^2$, such as from 0.1 $mm^2$ to 20.0 $mm^2$, such as from 1.0 $mm^2$ to 15.0 $mm^2$, such as from 1.0 $mm^2$ to 10 $mm^2$ and including 5.0 $mm^2$.

The current densities of the cathodes can typically range from about 0.05 $\mu A\, cm^{-2}$ to about 50 $\mu A\, cm^{-2}$, for example from about 0.1 $\mu A\, cm^{-2}\, mM^{-1}$ and about 20 $\mu A\, cm^{-2}\, mM^{-1}$. In general, the cathodes operate at temperatures between about 25° C. and about 45° C. The cathodes can operate in a biological fluid continuously or intermittently for a period longer than 1 hour, for example longer than 1 day, 3 days, 1 week, 2 weeks, 3 weeks or longer than 1 month.

In certain embodiments in which an inert substrate is used, the substrate is a non-conducting material, such as for example polymeric, plastic, glass, silicon-containing materials, dielectric materials, or ceramic materials, among other non-conducting materials. The substrate may be a flexible, deformable or thermoplastic substrate of polycarbonate, polyester (e.g., polyethylene terephthalate (PET)), polyvinyl chloride (PVC), polyurethane, polyether, polyamide, polyimide, combinations or copolymers thereof, such as glycol-modified polyethylene terephthalate. The substrate may be a rigid substrate to, for example, provide structural support against bending or breaking Examples of rigid materials that may be used as the substrate include low conductivity ceramics, such as aluminum oxide and silicon dioxide. A substrate may also have a varying rigidity along a dimension, e.g., length and/or width, of the substrate. In certain embodiments, the conductive ceria nanoparticles layer may be deposited onto a porous or microporous substrate. For example, the substrate may be formed, for example, as a mesh, a reticulated structure (e.g., reticulated graphite), a microporous film, or a film that is permeable to an analyte of interest. Likewise, the surface area of the substrate may further be increased by roughening. Where the surface of the cathode is roughened, the exposed surface area of the cathode may be greater than the geometric surface area to which the conductive ceria nanoparticles composition is applied. For example, the exposed surface area of a cathode which is roughened may be 2-fold or greater than the geometric surface area to which the ceria nanoparticle composition is applied, such as 3-fold or greater, such as 5-fold or greater, such as 10-fold or greater and including 25-fold or greater than the geometric surface area to which the ceria nanoparticle composition is applied.

As described above, in certain embodiments the ceria nanoparticle composition is combined with a conductive material to provide a conductive ceria nanoparticle composition for use as a cathode. For example, the ceria nanoparticle composition may be mixed with gold, carbon, platinum or other platinum group metal, platinum-carbon, doped-tin oxide, indium tin oxide, ruthenium, ruthenium dioxide, palladium, silver, nickel, rhodium, cobalt, titanium and combinations thereof.

In other embodiments, the ceria nanoparticle composition is deposited on a conductive substrate to form a cathode, such as needle or a wire. In some instances, the conductive substrate is a non-conductive substrate which has a conductive coating on the surface of the non-conductive substrate. Suitable conductive substrate and/or conductive coatings may include, but are not limited to gold, carbon, platinum or other platinum group metal, platinum-carbon, doped-tin oxide, indium tin oxide, ruthenium, ruthenium dioxide, palladium, silver, nickel, rhodium, cobalt, titanium and combinations thereof. Alternatively, the non-conducting cathode substrate may include a conductive polymer coating. Suitable conductive polymeric coatings include, but are not limited to conductive organic polymers, such as PEDOT (poly(3,4-ethylenedioxythiophene) or conductive polymers and copolymers of thiophene, or pyrrole, or acetylene that may be polycationic conductive polymers. Where the substrate is a conductive substrate (e.g., a conductive wire or needle), the ceria nanoparticle compositions may or may not further include a conductive material, depending on the desired conductivity of the resulting cathode. A cathode may include a plurality of conductive and nonconductive layers, where all of the materials may be the same or at least some may be different.

The ceria nanoparticle composition may be applied to at least a portion of one or more surfaces of a substrate to form a cathode. In some embodiments, the ceria nanoparticle composition is applied to at least a portion of at least 1 surface of the substrate. In other embodiments, the ceria nanoparticle composition is applied to 2 or more surfaces of the substrate, such as 3 or more surfaces of the substrate, such as 4 or more surfaces of the substrate and including 5 or more surfaces of the substrate. Compositions may be applied to at least a portion of all exposed surfaces. In certain embodiments, where the substrate is a planar substrate, ceria nanoparticle composition may be applied to all surfaces of the substrate to form the cathode.

As described above, the ceria nanoparticle composition may be applied to part or all of a surface of a substrate to form a cathode. In some embodiments, the ceria nanoparticle composition is applied to an entire surface of the substrate. In other embodiments, less than an entire surface of the substrate is applied with the ceria nanoparticle composition, such as 95% or less of the surface of the substrate is applied with the ceria nanoparticle composition, such as 75% or less, such as 50% or less, such as 25% or less, such as 10% or less, and including 5% or less, including 0.5%, of the surface of the substrate is applied with the ceria nanoparticle composition.

In certain embodiments, the overall length of the applied area may be no less than 0.01 mm and no greater than 5.0 mm. For example, the length may be between 0.05 mm and 4.5 mm, such as 0.1 mm to 4.0 mm, such as 0.15 mm to 3.0 mm and including 0.25 mm. It is understood, however that shorter and longer deposition areas may also suitable. In certain embodiments, the overall width of the applied area may be no less than 0.01 mm and no greater than 2.5 mm. For example, the width may be between 0.025 mm and 2.0 mm, such as 0.05 mm and 1.5 mm, such as 0.075 mm and 1.0 mm, including 0.1 mm. As such, the area of the cathode covered by the applied conductive ceria nanoparticle composition ranges from 0.0001 $mm^2$ to 12.5 $mm^2$, such as from 0.001 $mm^2$ to 10.0 $mm^2$, such as from 0.001 $mm^2$ to 9.0 $mm^2$, such as from 0.01 $mm^2$ to 7.5 $mm^2$ and including from 0.1 $mm^2$ to 5.0 $mm^2$.

As such, the geometrical areas of cathodes having the ceria nanoparticle composition may be between about 0.02 $mm^2$ and about 10 $mm^2$, for example between about 0.05 $mm^2$ and 5 $mm^2$ or between about 0.1 $mm^2$ and about 2 $mm^2$. The current densities of the cathodes may range from about 0.05 $\mu A\, cm^{-2}\, mM^{-1}$ and about 50 $\mu A\, cm^{-2}\, mM^{-1}$, such as from about 0.1 $\mu A\, cm^{-2}\, mM^{-1}$ and about 20 $\mu A\, cm^{-2}\, mM^{-1}$.

The conductive compositions may be applied to a surface of a substrate within an ink, such as a printing ink. Depending on the concentration of each component in the ceria nanoparticle composition, the dry volume of the composition employed to produce a cathode may vary, and may range from 1 μL to 250 μL such as from 2 μL to 200 μL such as 5 μL to 150 μL such as from 10 μL to 125 μL such as from 15 μL to 100 μL such as from 20 μL to 75 μL and including from 25 μL to 50 μL. When applied within an ink or by any other means in order to produce a cathode the mass of ceria nanoparticles employed in the cathode varies, ranging from 5 to 1000 mg of ceria nanoparticles, such as 10 mg to 750 mg, such as 25 mg to 500 mg, such as 50 to 250 mg, such as 75 mg to 150 mg and including 100 mg of ceria nanoparticles. The loading of ceria nanoparticles on the cathode substrate may range from 0.1 $mg/cm^2$ to 10 $mg/cm^2$, such as from 0.5 $mg/cm^2$ to 9 $mg/cm^2$, such as from 0.75 $mg/cm^2$ to 7.5 $mg/cm^2$, such as from 1 $mg/cm^2$ to 6.5 $mg/cm^2$ and including from 1.5 $mg/cm^2$ to 5 $mg/cm^2$.

The density of ceria nanoparticles on the cathode substrate may depend, in some instances on the physical properties of the composition, such as for example diameter of the ceria nanoparticles, the oxygen loading of the ceria nanoparticles and the concentration of ceria nanoparticles in the composition applied to the surface in order to form a cathode. In certain aspects, the area of the substrate on which the conductive ceria nanoparticles composition is applied includes between $10^2$ and $10^{15}$ ceria nanoparticles per $mm^2$. For example, the area of the substrate may include between $10^3$ and $10^{12}$ ceria nanoparticles per $mm^2$, between $10^4$ and $10^{10}$ ceria nanoparticles per $mm^2$, between $10^5$ and $10^8$ ceria nanoparticles per $mm^2$, including between $10^6$ and $10^7$ ceria nanoparticles per $mm^2$.

The average thickness of the layer of ceria nanoparticles composition of the cathode will depend on the number of layers applied as well as the amount of ceria nanoparticle composition employed. For example, one or more layers of the ceria nanoparticle composition may be applied to a substrate to form a cathode, such as two or more layers, such as three or more layers, such as 5 or more layers, and including 10 or more layers of the ceria nanoparticle composition may be applied to a substrate to form a cathode. The thickness of each layer may be the same or different, as desired. For example, where the thickness of each layer is different, the thickness of each layer of applied ceria nanoparticle composition may differ by 75% or less, such as 50% or less, such as 40% or less, such as 30% or less, such as 25% or less and including by 10% or less. Accordingly, the total thickness of the applied composition may be 0.1 μm or more, such as 0.5 μm or more, such as 1.0 μm or more, such as 1.5 μm or more, such as 2.0 μm or more, such as 5 μm or more, such as 10 μm or more, including 100 μm or more. Additional layers of ceria nanoparticle composition may be added if necessary, such as for example to increase the coulombic capacity and/or improve smoothness and uniformity of the ceria nanoparticle layer. For example, if after evaluating the deposited ceria nanoparticle layer, it is determined that the thickness of the ceria nanoparticle layer is less than targeted or is unsuitable, additional layers may be applied to all or part of the deposited ceria nanoparticle layer.

The total mass of applied ceria nanoparticles in each layer may vary depending on the size of the applied area on the cathode substrate as well as the number of layers applied. In certain instances, the total mass of ceria nanoparticles applied in each layer may be 10 mg or more, such as 25 mg or more, such as 50 mg or more, such as 75 mg or more, and including 100 mg or more. The density of ceria nanoparticles applied onto the substrate may be adjusted to achieve a desired mass per unit area i.e., loading of ceria nanoparticles on the substrate upon drying of the ceria nanoparticle composition. For example, the ceria nanoparticle number density may be chosen to achieve uniform distribution on the surface of the cathode, and also to provide less than a single layer of ceria nanoparticles on the surface of the substrate. In other embodiments, the ceria nanoparticle density may be chosen to achieve a particular oxygen loading on the cathode surface. In yet other embodiments, the ceria nanoparticle surface-density may be chosen to achieve 50% or greater coverage of the surface of the substrate, such as 75% or greater, such as 80% or greater, such as 85% or greater, such as 90% or greater, such as 95% or greater and including 99% or greater coverage of the surface of the cathode.

Cathodes employing the ceria nanoparticle compositions according to the present disclosure include an amount of absorbed oxygen loaded into the ceria nanoparticles, as described above. The amount of absorbed oxygen loaded into the nanoparticles may vary depending on the source of ceria, the number of lattice vacancies as well as the desired properties of the ceria nanoparticles. Absorbed oxygen can be, for example, molecular oxygen (i.e., $O_2$), bound superoxide radical anion (i.e., $.O_2^-$) or superoxide radical (.OOH). The amount of absorbed oxygen loaded into the subject ceria nanoparticles when employed in a cathode may be 0.1 percent by weight or more, such as 0.2 percent by weight or more, such as 0.3 percent by weight or more, such as 0.5 percent by weight or more, such as 1.0 percent by weight or more.

The coulombic capacity of cathodes employing the ceria nanoparticle compositions is 0.5 millicoulombs (mC) or greater, such as 2 mC or greater, such as 5 mC or greater and including 10 mC or greater. The coulombic capacity per $cm^2$ of cathodes employing the ceria nanoparticle compositions is 0.5 mC $cm^{-2}$ or greater, such as 1 mC $cm^{-2}$ or greater, such as 5 mC $cm^{-2}$ or greater, 10 mC $cm^{-2}$ or greater, such as 20 mC $cm^{-2}$ or greater, and including 50 mC $cm^{-2}$ i.e. 1 C $cm^{-2}$ or greater. Through binding of $O_2$ and through replenishing $Ce^{4+}$ by $O_2$-oxidation of $Ce^{3+}$ in periods when the electron current flowing to the ceria nanoparticles is low, the subject ceria nanoparticle compositions can serve as reservoir for electroreducible oxidant, available in periods when the electron current flow is high. As such, this electroreducible oxidant provides for smaller cathodes with higher current density and higher sensitivity. By "smaller cathodes" is meant cathodes which are smaller in size than cathodes which do not employ the ceria nanoparticle compositions, such as 90% of the size of a cathode which does not employ a ceria nanoparticle composition or smaller, such as 75% or smaller and including 50% or smaller than the size of a cathode which does not employ the subject ceria nanoparticle compositions. Likewise, by "higher current density" and "higher sensitivity" is meant a current density or sensitivity which is 10% or greater than the current density or sensitivity which can be achieved by cathodes which do not employ the ceria nanoparticle compositions, such as 25% or greater, such as 50% or greater, such as 100% or greater, such as 2-times or greater, and including 5-times or greater than the current density or sensitivity which can be achieved by cathodes which do not employ the ceria nanoparticle compositions. It can also provide for improved maintenance of the sensitivity at high glucose concentrations, for example at glucose concentrations higher than 15 mM, 20 mM, or 25 mM.

At least part of the ceria nanoparticles can be regenerated by reaction with oxygen dissolved in a body-fluid in cathodes. For example, the coulombic capacity of the oxygen-regenerated ceria nanoparticles may be greater than 0.5 millicoulombs (mC), such as greater than 5 mC, such as greater than 20 mC, such as greater than 20 mC and including greater than 100 mC. The electron accepting species of the cathode can be electroreduced at a current density exceeding 1 $\mu A\ cm^{-2}$, for example exceeding 10 $\mu A\ cm^{-2}$, for example exceeding 100 $\mu A\ cm^{-2}$ at potential between about +0.3 V and about −0.4 V versus the potential of a Ag/AgCl electrode (3 M KCl). The ceria nanoparticle composition can be electroreduced while glucose, dissolved in a fluid of the body (e.g., blood, interstitial fluid, etc.) is oxidized or electrooxidized. The ceria nanoparticle composition can be electroreduced when the cathode is poised at a potential positive of −0.4 V, −0.3 V or −0.2 V versus the potential of an Ag/AgCl electrode (3 M KCl). When the composition is electro-reduced, the Faradaic current density of the cathode may be 1 $\mu A\ cm^{-2}$ or greater, such as 10 $\mu A\ cm^{-2}$ or greater, such as 0.1 $mA\ cm^{-2}$ or greater, such as 0.2 $mA\ cm^{-2}$ or greater and including 0.5 $mA\ cm^{-2}$ or greater.

Ceria Nanoparticle Reference Electrodes

Aspects of the present disclosure also include reference electrodes having one or more of the subject ceria nanoparticle compositions. In certain embodiments, in order to form the reference electrode the ceria nanoparticle composition is deposited on surface of a conductive material (e.g., layered over the conductive material). In such embodiments, the conductive material may be deposited over an inert non-conducting substrate or over a conductive material coating of an inert non-conductive substrate or on the conductive material which may itself provide the structural support to act as an electrode while in use, such as, for example, a metallic needle or a wire. In some embodiments, in order to form the reference electrode the ceria nanoparticle composition is combined with a conductive material, for example mixed with the conductive material to provide a conductive ceria nanoparticle composition. The conductive ceria nanoparticle composition may alternatively be formed or shaped to provide the structural support to act as a reference electrode while in use, such as, for example, a needle or a wire.

In certain embodiments, the reference electrode includes a cerium nanoparticle composition that includes a mixed valence cerium nanoparticle composition. "Mixed valence" means that the nanoparticle lattices and/or their surfaces include both $Ce^{3+}$ and $Ce^{4+}$ cations as is the case in oxygen-deficient ceria, $CeO_{2-x}$. The lattice structure of the inner bulk of the mixed valence cerium nanoparticles can be partly, mostly, or entirely similar to that of crystalline ceria ($CeO_2$). Although macrocrystalline ceria is neither electroreduced nor electrooxidized in a neutral pH aqueous solution, for example in neutral pH 0.1 M NaCl, in a potential range within 0.3 V of that of the Ag/AgCl (3M KCl) electrode, $Ce^{4+}$ at or near the surface of the nanoparticles can be electroreduced and $Ce^3$ at or near the surface of the nanoparticles can be electrooxidized. The corresponding electrode potential associated with the reversible electrochemical reaction $Ce^{4+}+e^-\leftrightarrow Ce^{3+}$ of the surface or near surface bound ions can differ by less than 0.3 V from that of the Ag/AgCl (3 M KCl) electrode at about 25° C. The potential of the $CeO_{2-x}$ nanoparticles comprising electrode can differ from the potential of the Ag/AgCl (3 M KCl) electrode, for example, by less than 250 mV, or by less than 200 mV, or by less than 150 mV, or by less than 100 mV or by less than 60 mV.

Furthermore, the redox potential of the ceria nanoparticle comprising reference electrode can be about independent of pH, for example in the pH range of the analyzed fluids of the body. Additionally, unlike the potential-defining redox reaction of the Ag/AgCl electrode, which is $AgCl+e^- \leftrightarrow Ag+Cl^-$, the redox potential of the ceria nanoparticle comprising reference electrode can also be independent of the concentration of the chloride anion. The redox potential of the reference electrode comprising $CeO_{2-x}$ nanoparticles, for example in blood or subcutaneous fluid at about 25.0 can be near the potential of the Ag/AgCl (3M KCl) electrode, i.e. the electrochemical reaction of which is taught to be $Ag+Cl^- \leftrightarrow AgCl+e^-$. The potential of the ceria nanoparticle comprising reference electrode can differ by less than 300 mV from the potential of the Ag/AgCl also in the analyzed solution, for example it can differ by 0-300 mV, for example by 0-200 mV, or by 0-100 mV or by 0-60 mV from the potential of the Ag/AgCl (3 KCl) electrode potential. The similarity of potentials can facilitate the substitution of Ag/AgCl (a mixture of Ag and AgCl) in analyte sensors, for example in subcutaneously or dermally implanted sensors for continuous glucose monitoring, or in ex-vivo sensors of glucose and other analytes.

Certain embodiments can include compositions having cerium nanoparticles of the formula $CeO_{2-x}$ where x is 0.1 or greater, such as 0.15 or greater, such as 0.2 or greater, such as 0.25 or greater. Because of charge neutrality, missing oxide anions can be associated with the presence of $Ce^{3+}$ ions, for example at or near the surface of the nanoparticle.

For use in reference electrodes the $CeO_{2-x}$ nanoparticles can be heated to at temperature higher than about 200.0 or 300° C., for example to 400° C. Such heating may cause the nanoparticles to loose $O_2$ and can provide a more precisely defined electrode potential. For example, coating of an electrode with a mixture containing the cerium nanoparticles heated to 400° C., carbon black and polymer can provide an electrode with a potential of about 70 mV versus Ag/AgCl in 3 M KCl.

A reference electrode may be planar as well as non-planar, and the composition may be applied to an exterior surface, an interior surface or a combination of exterior and interior surfaces of a substrate.

In some embodiments, the reference electrode includes a layer of the ceria nanoparticle composition applied onto a surface of a substrate, where the substrate may be pre-coated with a non-corroding conductor. The non-corroding conductor can be or can comprise a conductive organic polymer such as PEDOT (poly(3,4-ethylenedioxythiophene) or a polymer or copolymer of thiophene, or a polymer or copolymer of pyrrole, or polymer of acetylene. The non-corroding conductor can also be carbon or gold. When the composition comprises also particles of a conductor like carbon it can be coated directly on an inert, non-conducting base material formed in the shape of, for example, a plate, tube or mesh. The ceria nanoparticle composition may be applied to a surface of the substrate by a variety of methods, including, for example, vacuum deposition, drop casting, spin casting, sputtering, printed on a flat surface or in an embossed or otherwise recessed surface, transferred from a separate carrier or liner, etched, or molded physical vapor deposition, plasma deposition, chemical vapor deposition and printing among other deposition methods. Suitable methods of printing include screen-printing, piezoelectric printing, ink jet printing, laser printing, photolithography, painting, gravure roll printing, transfer printing, and other known printing methods.

The reference electrode substrate may be any suitable size, as desired, having typically a length which ranges from 0.05 mm to 5.0 mm, such as from 0.1 mm to 4.5 mm, such as from 1.0 mm to 4.0 mm, such as from 1.5 mm to 3.0 mm and including 2.5 mm and a width which ranges from 0.05 mm to 5.0 mm, such as from 0.1 mm to 4.5 mm, such as from 1.0 mm to 4.0 mm, such as from 1.5 mm to 3.0 mm and including 2.5 mm. It is understood, however that shorter or longer lengths and narrower or wider widths may also suitable. The geometric area of the reference electrode substrate may range from 0.01 $mm^2$ to 25.0 $mm^2$, such as from 0.1 $mm^2$ to 20.0 $mm^2$, such as from 1.0 $mm^2$ to 15.0 $mm^2$, such as from 1.0 $mm^2$ to 10 $mm^2$ and including 5.0 $mm^2$.

In certain embodiments in which an inert substrate is used, the substrate can be a non-conducting material, such as for example polymeric, plastic, glass, silicon-containing materials, dielectric materials, or ceramic materials, among other non-conducting materials. In some embodiments, the substrate is a flexible, deformable or thermoplastic substrate of polycarbonate, polyester (e.g., polyethylene terephthalate (PET)), polyvinyl chloride (PVC), polyurethane, polyether, polyamide, polyimide, combinations or copolymers thereof, such as glycol-modified polyethylene terephthalate. In other embodiments, the substrate may be a rigid substrate such as aluminum oxide and silicon dioxide. A substrate may also have a varying rigidity along a dimension of the substrate. In certain embodiments, the ceria nanoparticles layer may be deposited onto a porous or microporous substrate. For example, the substrate may be formed, for example, as a mesh, a reticulated structure (e.g., reticulated graphite), a microporous film, or a film that is permeable to an analyte of interest.

As noted above, in certain embodiments, the ceria nanoparticle composition is combined with a conductive material to provide a conductive ceria nanoparticle composition for use as a reference electrode. For example, the ceria nanoparticle composition may include gold, carbon, platinum or other platinum group metal, platinum-carbon, doped-tin oxide, indium tin oxide, ruthenium, ruthenium dioxide, palladium, silver, nickel, rhodium, cobalt, titanium and combinations thereof.

In other embodiments, the ceria nanoparticle composition is deposited on a conductive substrate to form a reference electrode, such as needle or a wire. In some instances, the conductive substrate is a non-conductive substrate which has a conductive coating on the surface of the non-conductive substrate. Suitable conductive substrate and/or conductive coatings may include, but are not limited to gold, carbon, platinum or other platinum group metal, platinum-carbon, doped-tin oxide, indium tin oxide, ruthenium, ruthenium dioxide, palladium, silver, nickel, rhodium, cobalt, titanium and combinations thereof. Alternatively, the non-conducting reference electrode may include a conductive polymer coating. Suitable conductive polymeric coatings include, but are not limited to conductive organic polymers, such as PEDOT (poly(3,4-ethylenedioxythiophene) or conductive polymers and copolymers of thiophene, or pyrrole, or acetylene that may be polycationic conductive polymers. Where the substrate is a conductive substrate (e.g., a conductive wire or needle), the ceria nanoparticle compositions may or may not further include a conductive material, depending on the desired conductivity of the resulting reference electrode. A reference electrode may include a plurality of conductive and nonconductive layers, where all of the materials may be the same or at least some may be different.

The conductive ceria nanoparticle composition may be applied to one or more surfaces of a substrate to form a reference electrode. In some embodiments, the ceria nanoparticle composition is applied to at least a portion of at least one surface of the substrate. In other embodiments, the ceria nanoparticle composition is applied to two or more surfaces of the substrate, such as 3 or more surfaces of the substrate, such as 4 or more surfaces of the reference electrode substrate and including 5 or more surfaces of the substrate. In certain embodiments, where the reference electrode substrate is a planar substrate, ceria nanoparticle composition may be applied to up to all surfaces of the substrate to form the reference electrode.

The ceria nanoparticle composition may be applied to part or all of a surface of a substrate to form a reference electrode. In some embodiments, the ceria nanoparticle composition is applied to an entire surface of the substrate. In other embodiments, less than an entire surface of the substrate is applied with the ceria nanoparticle composition, such as 95% or less of the surface of the substrate is applied with the conductive ceria nanoparticle composition, such as 75% or less, such as 50% or less, such as 25% or less, such as 10% or less, and including 5% or less, including 0.5%, of the surface of the substrate is applied with the ceria nanoparticle composition.

In certain embodiments, the overall length of the applied area may be no less than 0.01 mm and no greater than 5.0 mm. For example, the length may be between 0.05 mm and 4.5 mm, such as 0.1 mm to 4.0 mm, such as 0.15 mm to 3.0 mm and including 0.25 mm. It is understood, however that shorter and longer deposition areas may also suitable. In certain embodiments, the overall width of the applied area may be no less than 0.01 mm and no greater than 2.5 mm. For example, the width may be between 0.025 mm and 2.0 mm, such as 0.05 mm and 1.5 mm, such as 0.075 mm and 1.0 mm, including 0.1 mm. As such, the area of the reference electrode covered by the applied ceria nanoparticle composition ranges from 0.0001 $mm^2$ to 12.5 $mm^2$, such as from 0.001 $mm^2$ to 10.0 $mm^2$, such as from 0.001 $mm^2$ to 9.0 $mm^2$, such as from 0.01 $mm^2$ to 7.5 $mm^2$ and including from 0.1 $mm^2$ to 5.0 $mm^2$.

When applied to a surface as an ink, for example a printing ink, then depending on the concentration of each component in the ceria nanoparticle composition, the amount of composition employed to produce a reference electrode may vary, and may range after the ink dries from 0.1 μL to 25 μL of the ceria nanoparticle composition, such as from 0.2 μL to 20 μl, such as 0.5 μL to 15 μL such as from 1 μL to 12.5 μL such as from 1.5 μL to 10 μL such as from 2.0 μL to 7.5 μL and including from 2.5 μL to 5.0 μl of the ceria nanoparticle composition. As such, the total mass of ceria nanoparticles applied to the reference electrode substrate varies, ranging from 0.5 to 100 mg of ceria nanoparticles, such as 1.0 mg to 75 mg, such as 2.5 mg to 50 mg, such as 5.0 to 25 mg, such as 7.5 mg to 15 mg and including 10 mg of ceria nanoparticles. Accordingly, the loading of ceria nanoparticles on the reference electrode substrate may range from 0.1 mg/$cm^2$ to 100 mg/$cm^2$, such as from 0.5 mg/$cm^2$ to 20 mg/$cm^2$, such as from 0.75 mg/$cm^2$ to 10 mg/$cm^2$, such as from 1 mg/$cm^2$ to 6.5 mg/$cm^2$ and including from 1.5 mg/$cm^2$ to 5 mg/$cm^2$.

The density of ceria nanoparticles on the substrate may depend, in some instances on the physical properties of the composition, such as for example diameter of the ceria nanoparticles and the concentration of ceria nanoparticles in the composition applied to the surface to form a reference electrode. In certain aspects, the area of the substrate on which the ceria nanoparticles composition is applied includes between $10^2$ and $10^{15}$ ceria nanoparticles per $mm^2$. For example, the area of the substrate may include between $10^3$ and $10^{12}$ ceria nanoparticles per $mm^2$, between $10^4$ and $10^{10}$ ceria nanoparticles per $mm^2$, between $10^5$ and $10^8$ ceria nanoparticles per $mm^2$, including between $10^6$ and $10^7$ ceria nanoparticles per $mm^2$.

The average thickness of the layer of ceria nanoparticles composition on the substrate will depend on the number of layers applied as well as the amount of ceria nanoparticle composition applied to the surface. In some embodiments, one or more layers of the ceria nanoparticle composition is applied to the substrate, such as two or more layers, such as three or more layers, such as 5 or more layers, and including 10 or more layers of the ceria nanoparticle composition are applied to the substrate. The thickness of each layer may be the same or different, as desired. For example, where the thickness of each layer is different, the thickness of each layer of applied ceria nanoparticle composition may differ by 75% or less, such as 50% or less, such as 40% or less, such as 30% or less, such as 25% or less and including by 10% or less. Accordingly, the total thickness of the applied composition may be 0.1 μm or more, such as 0.5 μm or more, such as 1.0 μm or more, such as 1.5 μm or more, such as 2.0 μm or more, such as 5 μm or more, such as 10 μm or more, including 100 μm or more. Additional layers of ceria nanoparticle composition may be added to the substrate if necessary, such as for example to improve smoothness and uniformity of the conductive ceria nanoparticle layer. For example, if after evaluating the deposited ceria nanoparticle layer, it is determined that the ceria nanoparticle layer is less than targeted or is unsuitable, additional layers may be applied to all or part of the deposited ceria nanoparticle layer.

Accordingly, the total mass of applied ceria nanoparticles in each layer will vary depending on the size of the applied area on the substrate as well as the number of layers applied. In certain instances, the total mass of ceria nanoparticles applied in each layer may be 10 mg or more, such as 25 mg or more, such as 50 mg or more, such as 75 mg or more, and including 100 mg or more. The density of ceria nanoparticles applied onto the reference electrode may be adjusted to achieve a desired mass per unit area of ceria nanoparticles on the reference electrode upon drying of the ceria nanoparticle composition. For example, the ceria nanoparticle number density may be chosen to achieve uniform distribution on the surface of the reference electrode, and also to provide less than a single layer of ceria nanoparticles on the surface of the substrate. In other embodiments, the ceria nanoparticle density may be chosen to achieve a particular redox potential of the reference electrode.

In certain embodiments, the reference electrode may further include a membrane. Suitable membranes can be but are not limited to a polymeric membrane, for example a neutral membrane comprising polyethylene glycol, a polyanionic membrane, like a membrane having sulfonate or carboxylate functions, or a zwitterionic polymeric membrane, such as a poly(2-vinyl pyridine sulfopropyl betaine) or poly(4-vinyl pyridine sulfopropyl betaine) comprising membrane.

The membrane may be applied to part or all of ceria nanoparticle composition on the surface of the reference electrode. In some embodiments, the protective membrane is applied to the entire surface of the ceria nanoparticle composition. In other embodiments, less than an entire surface of the ceria nanoparticle composition is applied with the protective membrane, such as 95% or less of the surface of the ceria nanoparticle composition is applied with the protective membrane, such as 75% or less, such as 50% or less, such as 25% or less, such as 10% or less, and including 5% or less of the surface of the ceria nanoparticle composition is applied with the protective membrane.

The redox potential of reference electrodes having the subject ceria nanoparticle compositions can be near the redox potential of a silver/silver chloride (Ag/AgCl) reference electrode in 3 M KCl. For example the absolute difference in the redox potentials of the reference electrode having the subject ceria nanoparticle compositions and an Ag/AgCl (3M KCl) electrode may be 0.3 V or less, such as 0.25 V or less, such as 0.20 V or less, such as 0.15 V or less, such as 0.1 V or less, such as 0.05 V or less. It can be, for example, within about 0.02 V or less versus the potential of Ag/AgCl at the chloride concentration in the subcutaneous fluid.

Ceria Nanoparticle Electrochemical Analyte Sensors

Aspects of the present disclosure also include electrochemical sensors employing a cathode and/or reference electrode employing one or more of the subject ceria nanoparticle compositions, such as in vivo analyte sensors.

The particular configuration of electrochemical sensors having one or more of a reference electrode and a cathode employing the subject ceria nanoparticle compositions may depend on the use for which the electrochemical sensor is intended and the conditions under which the electrochemical sensor will operate. In embodiments of the present disclosure, electrochemical sensors are in vivo wholly positioned electrochemical analyte sensors or transcutaneously positioned electrochemical analyte sensors configured for in vivo positioning in a subject. For example, at least a portion of an in vivo sensor may be configured to be positioned in the subcutaneous tissue or in the dermis for monitoring analyte concentrations in interstitial or dermal fluid.

A variety of analytes can be monitored in the body of a subject using the analyte sensors disclosed herein including, but not limited to, glucose, oxygen, pH, carbon dioxide, chloride, potassium, electrolytes, ketones, lactate, pyruvate, of body fluid. In certain embodiments, the analyte sensors of the present disclosure are glucose sensors.

The disclosed analyte sensors may include an analyte-responsive enzyme and a redox mediator. For example, a glucose oxidase (GOD) or glucose dehydrogenase (GDH) can be used when the analyte is glucose. A lactate oxidase can be used when the analyte is lactate. Hydroxybutyrate dehydrogenase can be used when the analyte is a ketone. In order to facilitate electrochemical reaction, the analyte sensor may further include an enzyme co-factor. For example, suitable cofactors include pyrroloquinoline quinone (PQQ), and flavin adenine dinucleotide (FAD).

In some embodiments, enzymes catalyze the electrolysis of an analyte by transferring electrons between the analyte and the electrode through a redox mediator. In one embodiment, the analyte-responsive enzyme is disposed on the anode. In certain embodiments, the analyte-responsive enzyme is immobilized on the anode by, for example, cross linking the analyte-responsive enzyme with a redox mediator on the anode, thereby providing a sensing layer on the anode. In an alternative embodiment, the analyte-responsive enzyme is disposed adjacent to the anode. Generally, the analyte-responsive enzyme and redox mediator are positioned in close proximity to the anode in order to provide for electrochemical communication between the analyte-responsive enzyme and redox mediator and the anode. Generally, the analyte-responsive enzyme and redox mediator are positioned relative to the cathode such that electrochemical communication between the analyte-responsive enzyme and the redox mediator and the cathode is minimized.

Additional analyte-responsive enzymes and cofactors which may be suitable with the analyte sensors disclosed herein are described in U.S. Pat. No. 6,736,957, the disclosure of which is herein incorporated by reference. In certain embodiments, the redox species is a transition metal compound or complex. The transition metal compounds or complexes may be osmium, ruthenium, iron, and cobalt compounds or complexes. Suitable redox mediators and methods for producing them are described in U.S. Pat. Nos. 5,262,035; 5,264,104; 5,320,725; 5,356,786; 6,592,745; and 7,501,053, the disclosure of each of which is herein incorporated by reference.

Examples of suitable in vivo electrochemical analyte sensors and methods for making them which may include one or more cathodes having a ceria nanoparticle composition as described herein include, but are not limited to, those described in U.S. Pat. Nos. 6,175,752, 6,134,461, 6,579,690, 6,605,200, 6,605,201, 6,654,625, 6,746,582, 6,932,894, 7,090,756, 5,356,786, 6,560,471, 5,262,035, 6,881,551, 6,121,009, 7,167,818, 6,270,455, 6,161,095, 5,918,603, 6,144,837, 5,601,435, 5,822,715, 5,899,855, 6,071,391, 6,377,894, 6,600,997, 6,514,460, 5,628,890, 5,820,551, 6,736,957, 4,545,382, 4,711,245, 5,509,410, 6,540,891, 6,730,200, 6,764,581, 6,503,381, 6,676,816, 6,893,545, 6,514,718, 5,262,305, 5,593,852, 6,746,582, 6,284,478, 7,299,082, 7,811,231, 7,822,557 and 8,106,780; U.S. Patent Application Publication Nos. 2010/0198034, 2010/0324392, 2010/0326842, 2007/0095661, 2008/0179187, 2008/0177164, 2010/0213057, 2011/0120865, 2011/0124994, 2011/0124993, 2010/0213057, 2011/0213225, 2011/0126188, 2011/0256024, 2011/0257495, 2012/0157801, 2012/0157801, 2012/0245447, and 2012/0323098.

In some embodiments, in vivo sensors may include an insertion tip positionable below the surface of the skin, e.g., penetrating through the skin and into, e.g., the subcutaneous or dermal space, in contact with the user's biological fluid such as interstitial fluid. Contact portions of an anode, a reference electrode and a cathode are positioned on the first portion of the sensor situated above the skin surface. An anode, a reference electrode and a cathode are positioned at the inserted portion of the sensor. Traces may be provided from the electrodes at the tip to a contact configured for connection with sensor electronics.

In certain embodiments, the anode and cathode of the sensor as well as the substrate and the dielectric layers are provided in a layered configuration or construction. For example, the sensor may include a substrate layer, and a first conducting layer such as a conductive polymer like PEDOT (poly(3,4-ethylenedioxythiophene), carbon, gold, etc., disposed on at least a portion of the substrate layer and which may provide the anode. A sensing layer may be positioned on the anode. A first insulation layer, such as a first dielectric layer can be disposed or layered on at least a portion of the first conducting layer and a second conducting layer may be positioned or stacked on top of at least a portion of the first insulation layer (or dielectric layer). The second conducting layer may also provide a reference electrode. A second insulation layer, such as a second dielectric layer may be positioned or layered on at least a portion of the second conducting layer. Further, a third conducting layer may be positioned on at least a portion of the second insulation layer and may provide the cathode. Finally, a third insulation layer may be disposed or layered on at least a portion of the third conducting layer. In this manner, the sensor may be layered such that at least a portion of each of the conducting layers is separated by a respective insulation layer (for example, a dielectric layer).

In other embodiments, some or all of the electrodes may be provided in a co-planar manner such that two or more electrodes may be positioned on the same plane (e.g., side-by side (e.g., parallel) or angled relative to each other) on the substrate. For example, co-planar electrodes may include a suitable spacing therebetween and/or include a dielectric material or insulation material disposed between the conducting layers/electrodes. Furthermore, in certain embodiments one or more of the electrodes may be disposed on opposing sides of the substrate. In such embodiments, electrical contact may be one the same or different sides of the substrate. For example, an electrode may be on a first side and its respective contact may be on a second side, e.g., a trace connecting the electrode and the contact may traverse through the substrate.

For in-vivo monitoring of a biochemical, but not necessarily for monitoring of pH or oxygen, or an electrolyte like chloride anion or potassium cation, a sensing layer which includes an analyte responsive enzyme and in certain embodiments a redox mediator, may be formed near or on a portion of the anode. The sensing layer formulation may include both an analyte responsive enzyme and a redox mediator, in some embodiments. The sensing layer may also include other components, such as, for example, a polymer and a bi-functional, short-chain, epoxide cross-linker, such as polyethylene glycol (PEG). A variety of different sensing layer configurations may be used. In certain embodiments, the sensing layer is deposited on the conductive material of an anode. The sensing layer may extend beyond the conductive material of the anode. In some cases, the sensing layer may also extend over other electrodes, e.g., over the cathode. In other embodiments the sensing layer is not deposited directly on the working electrode, but may be spaced apart from the anode and separated by a separation layer. A separation layer may include one or more membranes or films or a physical distance. The separation layer may also act as a mass transport limiting layer and/or an interferent eliminating layer and/or a biocompatible layer.

In vivo electrochemical analyte sensors according to certain embodiments may be configured to operate at low to zero oxygen concentration. By low oxygen concentration is meant the concentration of oxygen is 1.5 mg/L or less, such as 1.0 mg/L or less, such as 0.75 mg/L or less, such as 0.6 mg/L or less, such as 0.3 mg/L or less, such as 0.25 mg/L or less, such as 0.15 mg/L or less, such as 0.1 mg/L or less and including 0.05 mg/L or less. By zero oxygen concentration is mean the concentration of oxygen is 0.0 mg/L.

Methods for In-Vivo Monitoring of an Analyte Concentration

The electrochemical sensors described herein find use in methods for monitoring the concentration of an analyte in a fluid of the body of a subject. Generally, these methods include contacting the monitored fluid with the sensor, generating a sensor signal at the working electrode, and monitoring the concentration of the analyte using the sensor signal. It will be understood that the subject methods employ any one or more of the cerium nanoparticle compositions, electrodes, and sensors described herein.

A variety of approaches may be employed to determine the concentration of the analyte. In certain aspects, an electrochemical analyte concentration monitoring approach is used. For example, monitoring the concentration of the analyte using the sensor signal may be performed by amperometric, voltammetric, potentiometric, or any other convenient electrochemical monitoring technique.

Once an analyte concentration is determined, it may be displayed, stored, and/or otherwise processed to provide useful information. As demonstrated herein, the methods of the present disclosure are useful in connection with a device that is used to measure or monitor an analyte (e.g., glucose), such as any such device described herein. These methods may also be used in connection with a device that is used to measure or monitor another analyte, including oxygen, carbon dioxide, electrolytes, or other moieties of interest, for example, or any combination thereof, found in a bodily fluid, including subcutaneous e.g. interstitial fluid, dermal fluid, blood or other bodily fluid of interest or any combination thereof.

Methods for using an in vivo electrochemical analyte sensor may include positioning at least a portion of an electrochemical sensor beneath a skin surface of a user, for example, into a site such that subcutaneous fluid, dermal fluid, or blood comes into contact with the sensor (e.g. subcutaneous or dermal tissue or blood vessel). The sensor operates to electrolyze an analyte of interest in the biological fluid such that a current is generated between the anode and the cathode. A value for the current associated with the anode is determined. If multiple anodes are used, current values from each of the anodes may be determined. A microprocessor may be used to collect these determined current values or to further process these values.

The electrochemical sensor may be positionable in a user for determining the level of an analyte in the user's biological fluid. The analyte measurement data may be received continuously, periodically, or intermittently, for example. The analyte measurements may be received, for example, by an analyte monitoring device or system. The sensor response may be correlated and/or converted to analyte levels in blood or other fluids. Embodiments of the analyte sensors may be configured for monitoring the level of the analyte over a time period which may range from seconds, minutes, hours, days, weeks, to months, or longer.

In certain embodiments, the electrochemical analyte sensors are capable of in vivo detection of an analyte for one hour or more, e.g., a few hours or more, e.g., a few days or more, e.g., three or more days, e.g., five days or more, e.g., seven days or more, e.g., several weeks or at least one month or more. Future analyte levels may be predicted based on information obtained, e.g., the current analyte level at time zero as well as the rate of change of the analyte.

EXPERIMENTAL

The following examples are offered by way of illustration and not by way of limitation.

In this Experimental section, the term Ag/AgCl potential means the half-cell potential of the Ag/AgCl (3 M KCl) electrode at the temperature of the experiments, which was the ambient temperature of an air-conditioned laboratory, usually 23° C.±3° C. Also unless otherwise specified the experiments were carried out in the ambient laboratory atmosphere, i.e. under air.

Example 1

Ceria Nanoparticle Compositions

Composition 1:

A conductive ceria nanoparticle composition was produced from graphite and 10-20 nm particle size $CeO_{2-x}$ and an aqueous solution of trifluoroacetic acid (TFA). To 100 mg of graphite, 0.5 mL of an aqueous solution of TFA (0.1 w/v %) was added so that the carbon was well wetted by the solution. The wetting required 2 minutes. Next, 0.5 mL of the aqueous 0.1 w/v % TFA solution and 0.5 mL of colloidal $CeO_{2-x}$ (with acetate counterion, $CeO_2(OAc)$) were added and the mixture was ground for 20 minutes. An additional 0.5 mL of the aqueous 0.1 w/v % TFA solution was added and the mixture was ground for an additional 5 minutes.

Composition 2:

A conductive ceria nanoparticle composition was produced from graphite and 10-20 nm particle size $CeO_{2-x}$ and an aqueous solution of hydrochloric acid (HCl). To 100 mg of graphite, 0.5 mL of an aqueous solution of HCl (0.1 N) was added so that the carbon was well wetted by the solution. The wetting required 2 minutes. Next, 0.5 mL of the aqueous 0.1 N HCl solution and 0.5 mL of colloidal $CeO_2$, (with acetate counterion, $CeO_2(OAc)$) were added and the mixture was ground for 20 minutes. An additional 0.5 mL of the aqueous 0.1 N HCl solution was added and the mixture was ground for an additional 5 minutes.

Composition 3:

A conductive ceria nanoparticle composition was produced from graphite and 10-20 nm particle size $CeO_{2-x}$ and an aqueous solution of perfluorooctanoic acid (PFOA). To 100 mg of graphite, 0.5 mL of an aqueous solution of PFOA (0.1 w/v %) was added so that the carbon was well wetted by the solution. The wetting required 2 minutes. Next, 0.5 mL of the aqueous 0.1 w/v % of PFOA solution and 0.5 mL of colloidal $CeO_{2-x}$ (with acetate counterion, $CeO_2(OAc)$) were added and the mixture was ground for 20 minutes. An additional 0.5 mL of the aqueous 0.1 w/v % PFOA solution was added and the mixture was ground for an additional 5 minutes.

Composition 4:

A conductive ceria nanoparticle composition was produced from graphite and 10-20 nm particle size $CeO_{2-x}$ and an aqueous solution of acetic acid (PFOA). To 100 mg of graphite, 0.5 mL of an aqueous solution of acetic acid (0.1 w/v %) was added so that the carbon was well wetted by the solution. The wetting required 2 minutes. Next, 0.5 mL of the aqueous 0.1 w/v % of acetic acid solution and 0.5 mL of colloidal $CeO_{2-x}$ (with acetate counterion, $CeO_2(OAc)$) were added and the mixture was ground for 20 minutes. An additional 0.5 mL of the aqueous 0.1 w/v % acetic acid solution was added and the mixture was ground for an additional 5 minutes.

Figure 3:
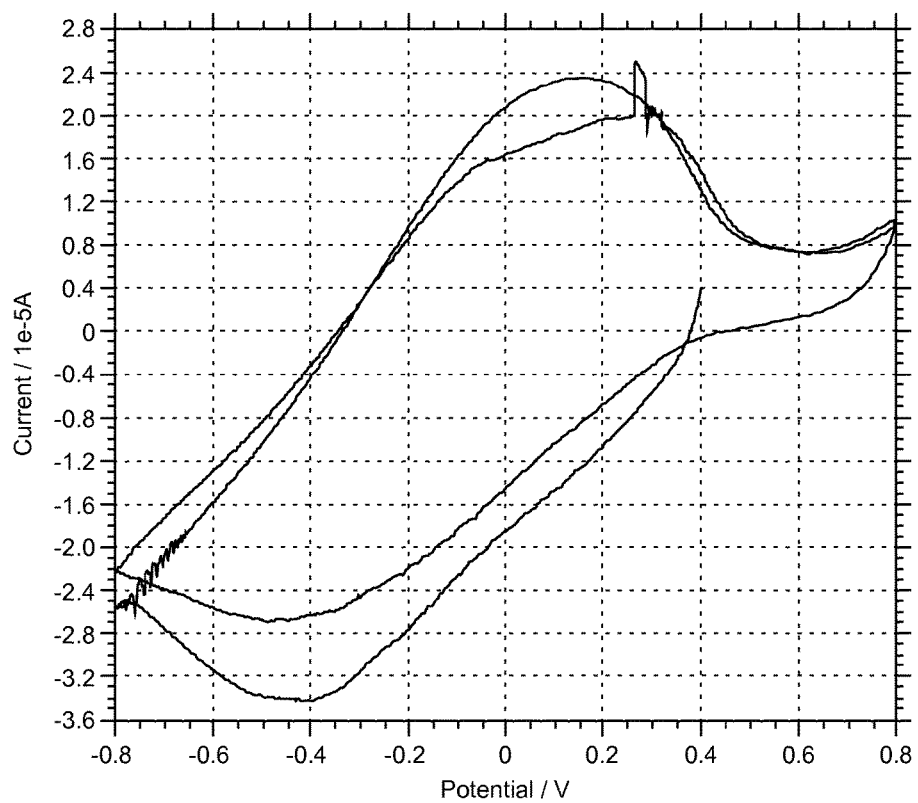
FIG. 3 shows an example cyclic voltammogram of an electrode system which includes an electrode employing a ceria nanoparticle composition.

Voltammetry and Chronoamperometry Studies:

Voltammetry and chronoamperometry studies were performed and showed that reduction currents increased with $O_2$ partial pressure. An exemplary cyclic voltammogram of a 0.25 $cm^2$ electrode having a coating of the conductive ceria nanoparticle composition as described below is illustrated in FIG. 3. A 5 μL drop of the conductive ceria nanoparticle composition was applied to the surface of a conductive polymer, aerated in 10 mM $KNO_3$. Cyclic voltammetry was performed with a platinum-wire counter-electrode and Ag/AgCl reference electrode with a scan rate of 1 mV/s.

Electrodes having a coating of the conductive ceria nanoparticle composition were also tested by cyclic voltammetry using a 3-electrode cell, fresh pencil lead counter-electrode, Ag/AgCl reference electrode at pH 7.2, 0.1 M NaCl, 20 mM phosphate buffer solution. The conductive ceria nanoparticle composition was applied to the rough printable side of a polyester sheet. Both uncured and cured electrodes were measured by cyclic voltammetry. Uncured electrodes were dried at room temperature overnight. Cured electrodes were heat cured at 100° C. for the following periods: ceria nanoparticle-TFA, 5 hours; ceria nanoparticle-HCl, 3.5 hours, ceria nanoparticle-cetyl trimethylammonium bromide (CTAB), overnight.

Figure 4:
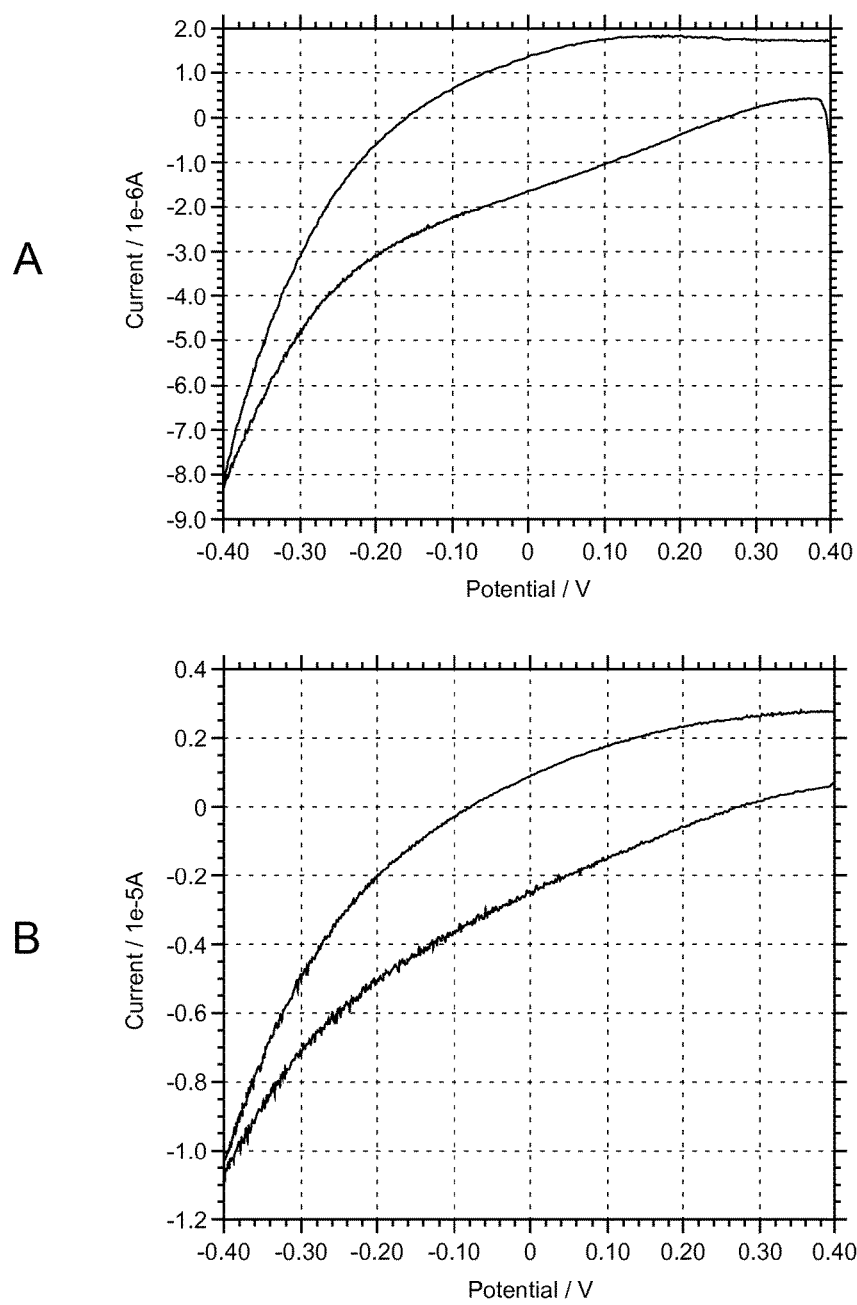
FIGS. 4A-B show cyclic voltammograms from electrode systems which include cured and uncured electrodes employing a ceria nanoparticle composition having, prior to their curing but not after curing, trifluoroacetic acid.
Figure 5:
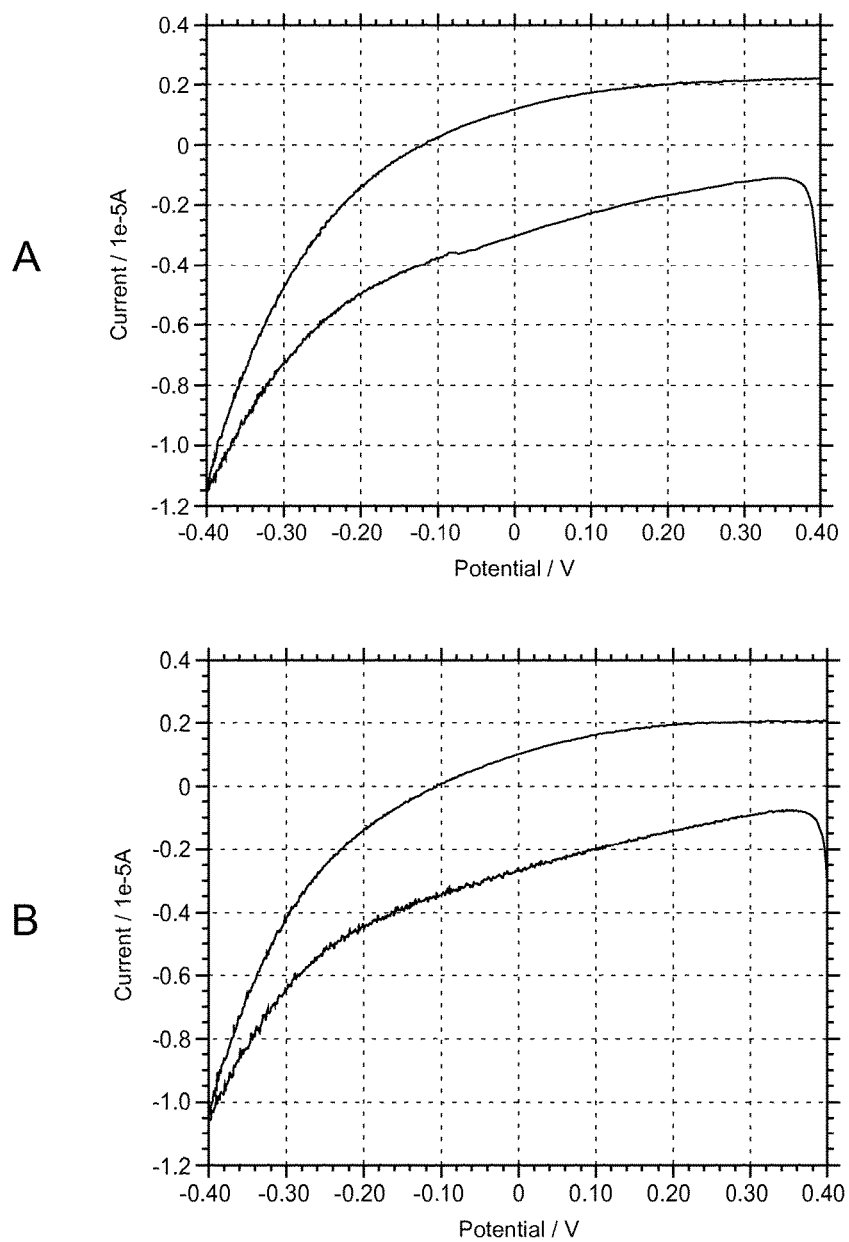
FIGS. 5A-B show cyclic voltammograms from electrode systems which include cured and uncured electrodes employing a ceria nanoparticle composition having hydrochloric acid.
Figure 6:
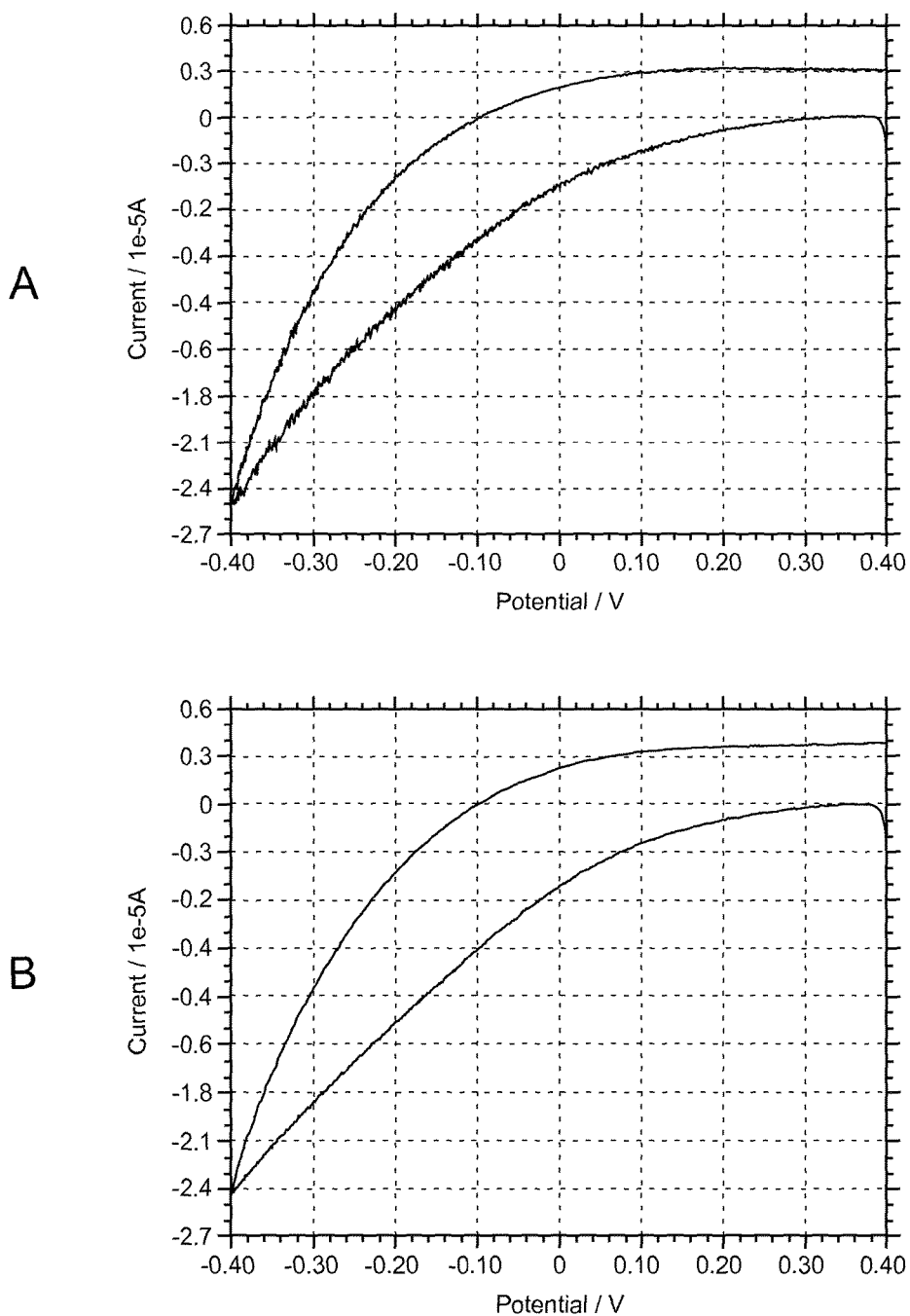
FIGS. 6A-D show cyclic voltammograms from electrode systems which include cured and uncured electrodes employing a conductive ceria nanoparticle composition having cetyl trimethylammonium bromide.
Figure 6:
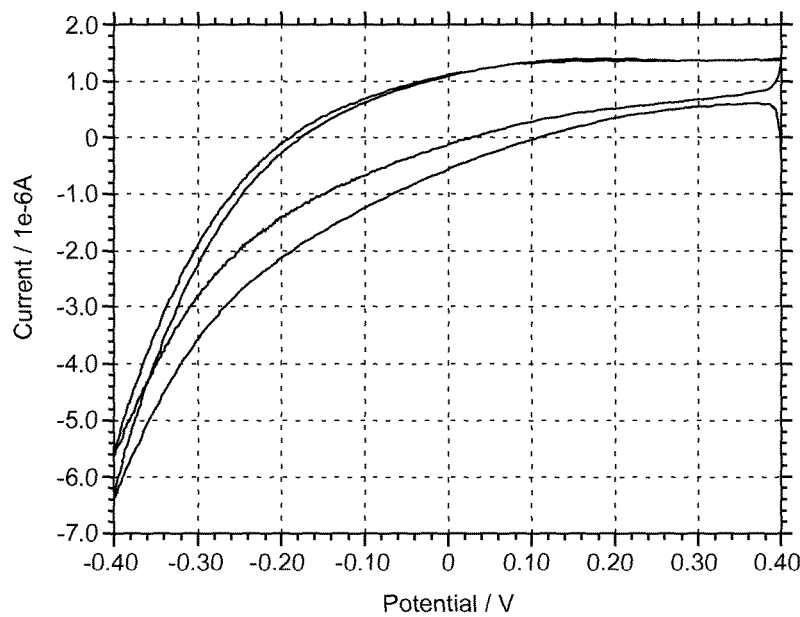
Figure 6:
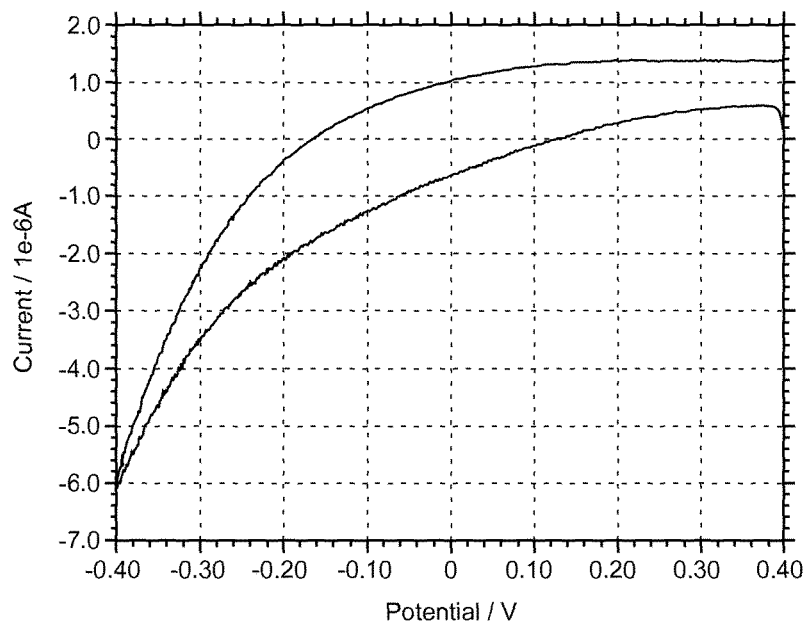

FIGS. 4-6 depict cyclic voltammograms for cured and uncured electrodes. FIGS. 4A and 4B depict cyclic voltammograms for uncured and cured electrodes, respectively, having a coating of the ceria nanoparticle-TFA composition diluted with water at a 1:1 ratio. FIGS. 5A and 5B depict cyclic voltammograms for uncured and uncured electrodes, respectively, having a coating of the ceria nanoparticle-HCl composition diluted with water at a 1:2 ratio. FIGS. 6A and 6B depict cyclic voltammograms for cured and uncured electrodes, respectively, having a coating of the ceria nanoparticle-CTAB composition diluted with water at a 1:1 ratio. FIGS. 6C and 6D depict cyclic voltammograms for cured and uncured electrodes, respectively, having a coating of the ceria nanoparticles-CTAB composition diluted with water at a 4:7 ratio.

Storage of Oxygen

A conductive ceria nanoparticle composition as prepared in Example 4 above was allowed to dry in an open dish at ambient temperature and atmosphere. The resulting powder was subjected to thermogravimetric analysis (TGA). The percentage of the weight lost was monitored while the powder was heated. Subsequently, $O_2$ gas was passed for 10 min through the composition before it was allowed to dry at ambient temperature and atmosphere. FIG. 1 illustrates that the powder from the oxygenated ceria nanoparticle composition above about 300° C. lost about 0.65% more of its weight than non-oxygenated ceria nanoparticle composition. Based on a molar mass of 172 g/mol for ceria and 32 g/mol for oxygen and since most the weight difference may be attributed to the binding of oxygen, 3.5 moles of oxygen per mole of ceria are bound in non-oxygenated ceria nanoparticles and 5.4 moles of oxygen per mole of ceria are bound in oxygenated ceria nanoparticles.

Cathodes Having a Coating of a Conductive Ceria Nanoparticle Composition

Figure 2:
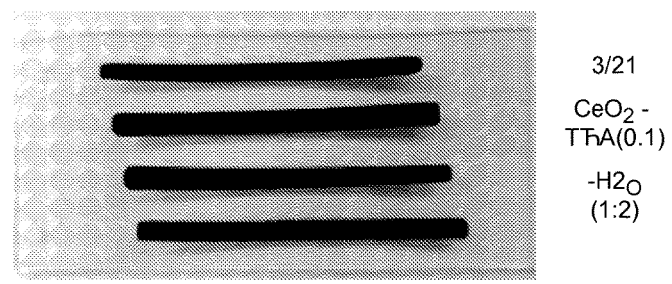
FIG. 2 shows an example of a cathode employing a conductive ceria nanoparticle composition.

Cathodes having a coating of the conductive ceria nanoparticle composition described above were produced by drop-coating 30 μl of the conductive ceria composition on a 2.5 mm×34 mm (about 0.8 $cm^2$) printable rough-side polyester strip. FIG. 2 shows an example of a cathode coated with a conductive ceria nanoparticle composition made with the composition of Example 1 (with acetate as counter-ion) and carbon, with 0.1 w/v % TFA.

Redox Potential of Cathodes Having Coatings of Polymer-Comprising Ceria Nanoparticle Compositions for In-Vivo Use.

When the ceria nanoparticles are bound within a polyethylene glycol diglycidyl ether-cross-linked poly-N-vinyl imidazole film the redox potential is about 58±15 mV versus that of Ag/AgCl (3M KCl) electrode, close to that of the Ag/AgCl cathode and to that close of the reference Ag/AgCl electrode.

Electroreduction of Ceria and of Dissolved Oxygen

Poly-N-vinylimidazole was prepared by polymerizing N-vinylimidazole (see e.g., Ohara et al. *Anal. Chem.* 1993, 65, 3512-3517). Polyethyleneglycol diglycidyl ether (PEGDGE) was used as a crosslinking agent. Carbon powder was made hydrophilic by exposing it to a low-pressure air-plasma for 10 min. Acetic acid-stabilized 20 wt %, pH 3 colloidal ceria nanoparticles (see e.g., composition Example 4 above) was oxygenated by passing through it $O_2$ for 10 minutes.

A conductive ceria nanoparticles composition was prepared by homogenizing a mixture of 1.0 mL of deionized water with 150 mg of the hydrophilic carbon, 1 mL of the oxygenated ceria nanoparticles by grinding in an agate mortar for about 20 minutes. 1.5 mL of the composition was then mixed with 1.5 mL of an aqueous 1.0 wt % poly-N-vinylimidazole solution and the mixture was ultrasonicated for 20 minutes, then mixed with 3.0 mL of water containing 4 μL PEGDGE.

Carbon electrodes of 5 mm diameter, having a surface area of 0.78 cm$^2$ were coated by applying a 2 μL drop of the above paste to the surface of the carbon electrodes. After drying the resultant film, a second 2 μL drop was applied on top of the dried film. After drying at ambient temperature for 6 hours, the coating was cured at 70° C. for 10 minutes.

Figure 7:
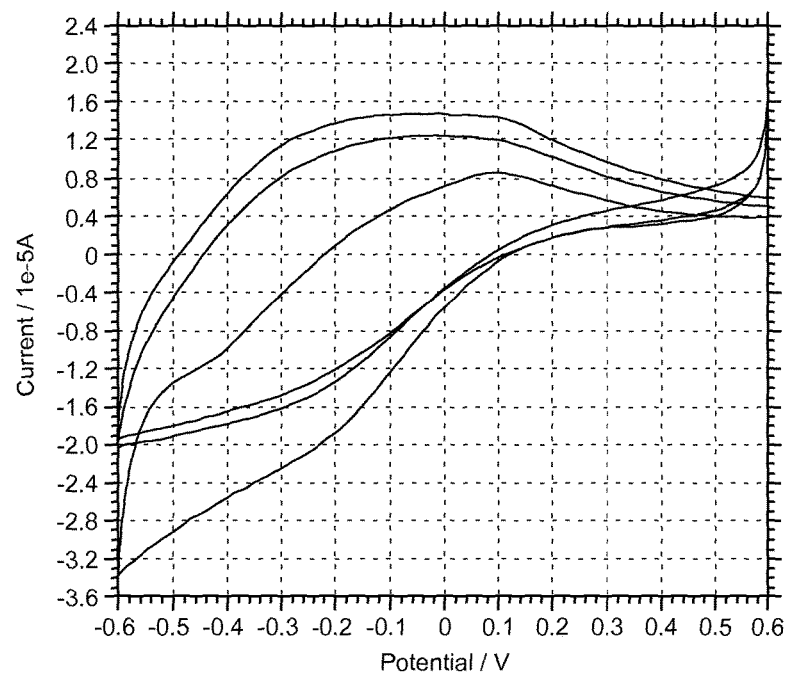
FIG. 7 shows a cyclic voltammogram from an electrode system having a cathode made by coating a plastic strip with a conductive ceria nanoparticle composition having a conductive polymer.

FIG. 7 depicts voltammograms measured at 1 mV/s scan rate in a three-electrode cell, equipped with a platinum wire counter-electrode and an Ag/AgCl reference electrode. Current is reported in amperes. (i.e., 1×10$^{-5}$ A is equal to 10 microamperes). The blue voltammogram was observed when nitrogen was passed through the cell; the red voltammogram was observed when air was passed; and the brown voltammogram was observed when oxygen was passed.

Electroreduction of ceria was observed at the potential of the Ag/AgCl reference electrode (i.e., 0 V). The cathodic (i.e., electroreduction current) increased at more reducing potentials. The cathodic electroreduction current were higher under air than under nitrogen, and were higher under oxygen than under air. Therefore, oxygen increases the cathodic current, which is associated with electroreduction of ceria nanoparticles.

Electrode Operation in Serum

Figure 8:
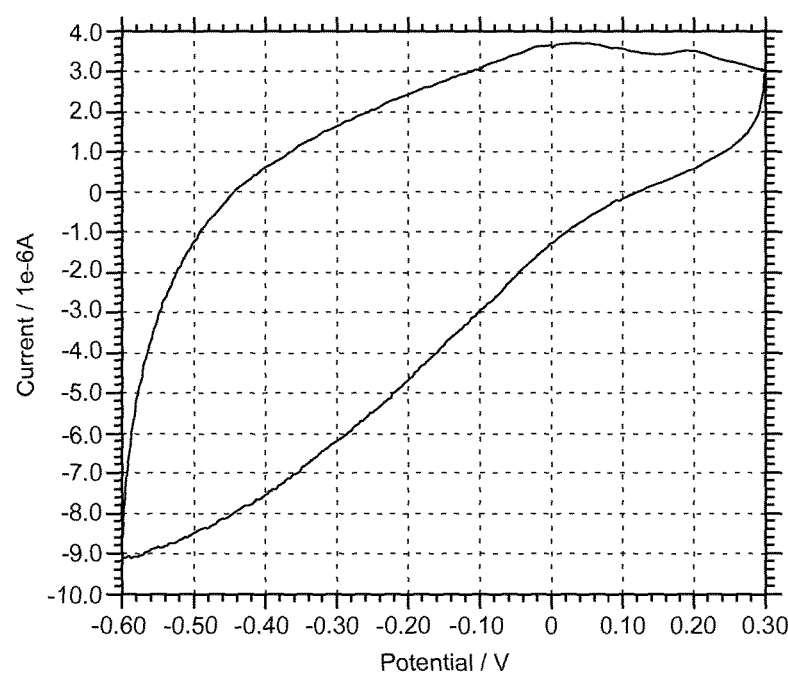
FIG. 8 shows a cyclic voltammogram in calf serum from electrode system having a cathode made by coating a plastic strip with a conductive ceria nanoparticles composition having a conductive polymer.

FIG. 8 shows a 1 mV/s scan rate cyclic voltammogram of the above electrode measured when the electrolyte in the cell was newborn calf serum and the atmosphere was air. Electroreduction was observed at all potentials negative of the potential (reducing) of the Ag/AgCl reference electrode.

Stability of the Electroreduction Current

Figure 9:
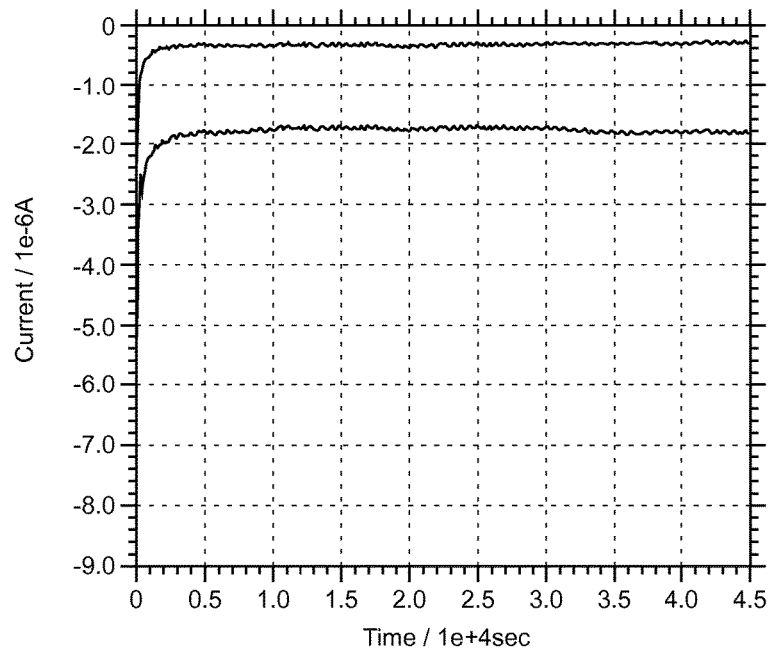
FIG. 9 shows the persistence of the electroreduction current of an electrode system made by coating a vitreous carbon electrode with a conductive ceria nanoparticles composition having a conductive polymer.

FIG. 9 shows the persistence of the electroreduction current of a 3 mm diameter vitreous carbon electrode coated with a mixture having conductive carbon, ceria nanoparticles, and poly-N-vinylimidazole crosslinked with polyethylene glycol diglycidyl ether in a solution under air. The electrolyte contained 20 mM imidazole and its pH was 7. The upper curve (i.e., curve located at about 0.5 microamperes) is for an electrode poised at the potential of the Ag/AgCl electrode (3 M KCl). The lower curve (i.e., curve located at about 2 microamperes) is for the same electrode poised at −0.2 V versus the potential of the Ag/AgCl electrode (3 M KCl).

Example 2

Reference Electrode Having a Coating of the Ceria Nanoparticle Composition

Ceria Nanoparticle Compositions:

20 wt %, pH 3.5, 10-20 nm particle size, acetic acid-stabilized colloidal ceria sol was purchased from Nyacol Nano Technologies, Ashland, Mass. For experiments requiring acetate-free and partially deoxygenated ceria, the sol was placed in an open Petri dish, where its water was allowed to evaporate and the residual powder was heated, increasing its temperature by 10° C./min to 400° C., then held at 400° C. for 4 h. For experiments requiring oxygenated ceria, O$_2$ was passed for 10 min through the ceria sol. Hydrophilic graphitic carbon: Timcal C-45, from Timcal, Westlake, Ohio was made hydrophilic by plasma treatment for 10 min in ~1 Torr air plasma.

A Plasma Cleaner of Harrick Plasma Ithaca, N.Y. 14850 was used for plasma treatment of the carbon and a Perkin-Elmer TGA-7 was used for the thermogravimetric analysis. The electrochemical experiments were performed with a Model 832, CHI (Austin, Tex.), potentiostat in a 3-electrode electrochemical cell with a 3 mm or a 2 mm diameter vitreous carbon working electrode; an Ag/AgCl (3M KCl) reference electrode; and a platinum wire or carbon rod counter-electrode. When the electrodes were rotated, a Pine Instrument rotator was used.

Electrodes without Carbon Particles:

1 mL of the ceria sol was diluted with 19 mL of deionized water; 2 mL of the diluted sol was mixed with 0.2 mL of 1 wt. % aqueous PVI and with 2 μL (undiluted) PEGDGE. 2 μL of the mixture was applied to the 3 mm diameter vitreous carbon electrodes. The resulting film was cured overnight in ambient air and temperature.

Electrodes with Carbon Particles:

200 mg of the calcined ceria nanoparticles was mixed with 100 mg of plasma-treated hydrophilic graphitic carbon and dry-ground in an agate mortar, then 2 mL water was added and the paste was re-ground for 10 min. 1.5 mL of the paste was mixed with 1.5 mL of 1 wt. % aqueous PVI, sonicated for 20 min, then mixed with 3 mL of water containing 4 μL PEGDGE. Vitreous carbon electrodes of 3 mm diameter were coated with 2 μL of the resulting paste and the films were cured overnight at ambient temperature. The same composition was used when films resisting a high stress were required for the 300-1000 rpm rotating disk experiments, except that 1 mL of the paste was mixed with 1 mL of 1 wt. % PVI and 2 μL PEGDGE. For the experiments in phosphate buffer a mixture of 1.0 mL of DI water, 150 mg of the hydrophilic carbon and 1 mL of oxygenated ceria sol was ground in an agate mortar for 20 min, then 1.5 mL of the paste was mixed with 1.5 mL of 1 wt. % aqueous PVI, sonicated for 20 min, then mixed with 3 mL of water containing 4 μL PEGDGE. Vitreous carbon electrodes of 3 mm diameter were coated by 2 μL droplets of the resulting paste and cured overnight at room temperature.

Glucose Sensors:

The sensors were similar to those described by Feldman et al. (Diabetes Technol. Ther. 2003, 5, 769). Printed carbon or sputtered gold traces formed the conducting bases of the electrodes. The working electrode contained cross-linked glucose oxidase and redox-polymer, over-coated with a glucose flux limiting membrane. The current was monitored with a custom-built potentiostat at an applied potential of 40 mV versus the reference electrode.

Figure 10:
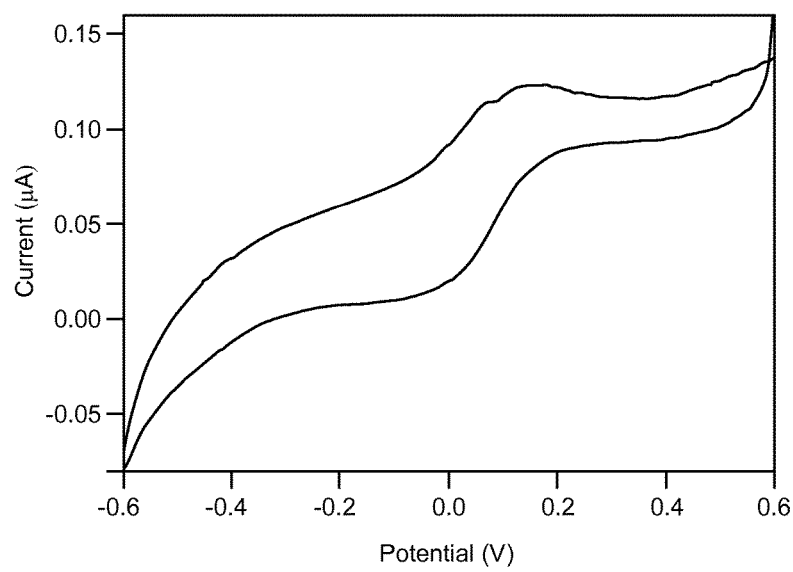
FIG. 10 shows a cyclic voltammogram of a vitreous carbon electrode coated with a film of ceria nanoparticles immobilized in PEGDGE crosslinked PVI.
Figure 11:
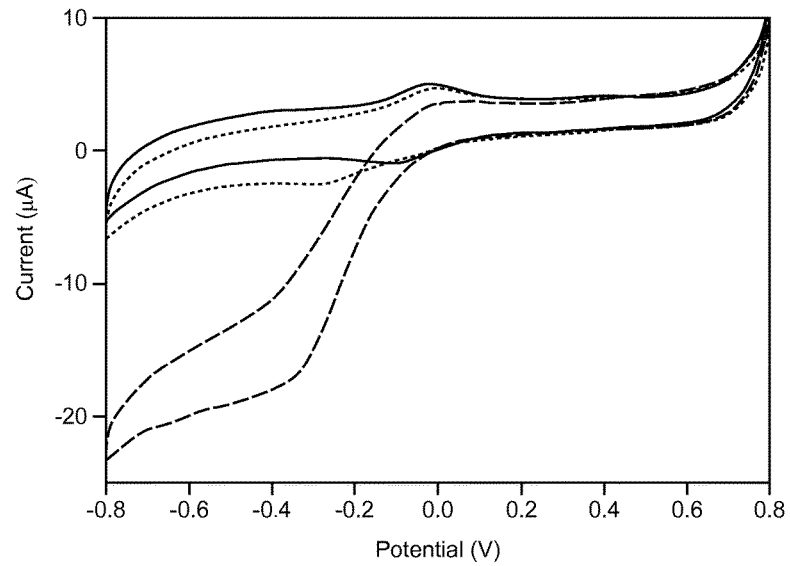
FIG. 11 shows a cyclic voltammograms of a vitreous carbon electrode coated with a film made of partially deoxygenated ceria nanoparticles, hydrophilic carbon particles and PEGDGE-crosslinked PVI under $N_2$, air, and $O_2$.

FIG. 10 shows the voltammogram of a 3 mm diameter vitreous carbon electrode coated with a film made with a sol of 10-20 nm CeO$_{2-x}$ particles immobilized in PEGDGE crosslinked poly-N-vinylimidazole (PVI) (pH 7, 20 mM imidazole-HCl buffer; under N$_2$; 1 mV/s scan rate). When applied to 3 mm vitreous carbon disks, the film withstood the shear stress resulting of rotation at 1000 rpm. The redox potential of the immobilized nanoparticles was 0.07 V vs. Ag/AgCl (3M KCl), nearly identical with the redox potential of Ag/AgCl in a physiological saline solution, where the Cl$^-$ concentration is about 20 times lower. When only a minute current is drawn of the reference electrode, this simple but resistive film suffices. For applications requiring greater current, the resistance of the films was reduced by incorporating hydrophilic graphitic carbon particles. Their incorporation increases the current density about fiftyfold without substantially altering the redox potential. FIG. 11 shows a cyclic voltammograms of a 3 mm vitreous carbon electrode coated with a film made of partially deoxygenated ceria nanoparticles, hydrophilic carbon particles and PEGDGE-crosslinked PVI under N$_2$ (solid line); air (dotted line) and O$_2$ (dashed line) (pH 7 imidazole-HCl buffer; 5 mV/s scan rate). In the experiment of FIG. 11, where the CeO$_{2-x}$ nanoparticles were deoxygenated by heating to 400° C., the redox potential under N$_2$ was 60 mV versus Ag/AgCl (3M KCl), i.e. about 10 mV versus Ag/AgCl in physiological saline buffer; under air it downshifted, but only by 40 mV and under $O_2$ it was downshifted by 90 mV. The potential under $N_2$ was pH-independent. Under $O_2$ the potential depended on pH. In air the pH dependence was, however, slight (FIG. 11).

Figure 12:
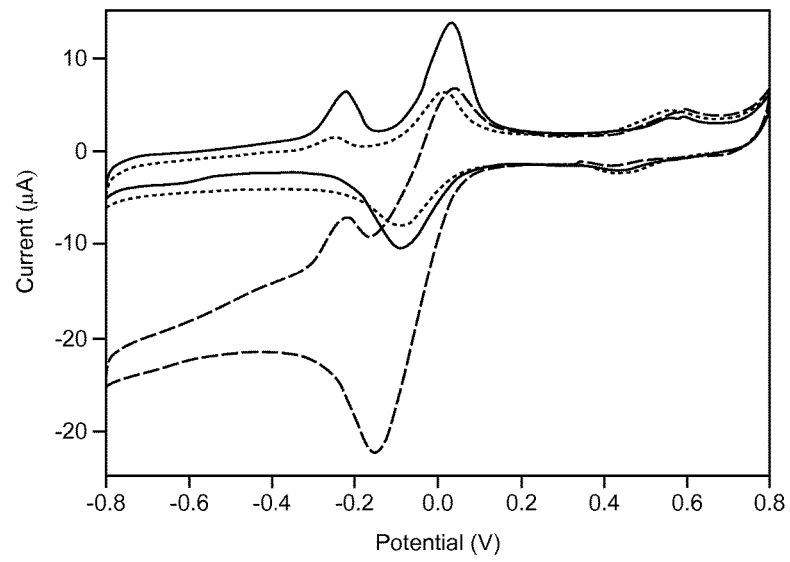
FIG. 12 shows a cyclic voltammograms of a vitreous carbon electrode coated with a film made of partially deoxygenated ceria nanoparticles, carbon and PEGDGE-crosslinked PVI under $N_2$, air and $O_2$.
Figure 13:
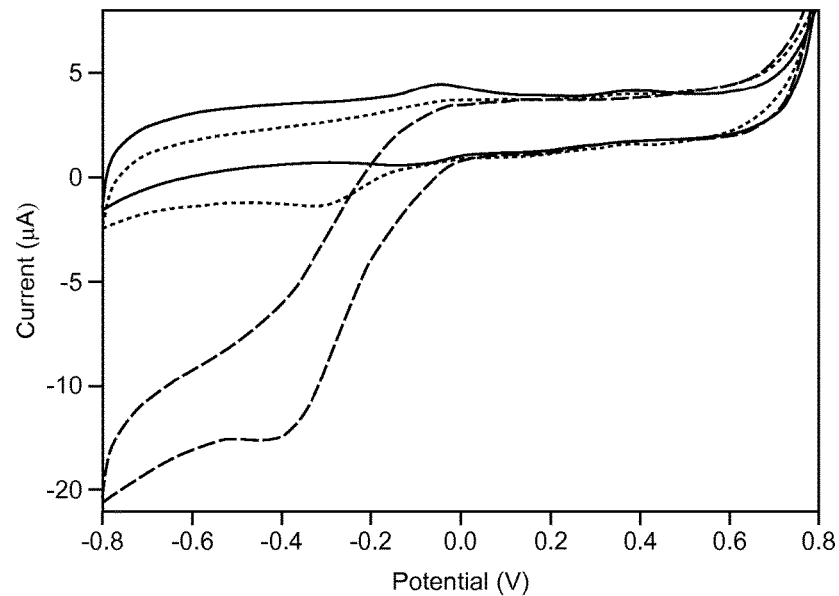
FIG. 13 shows a cyclic voltammograms of a vitreous carbon electrode coated with a film made of partially deoxygenated ceria nanoparticles, carbon and PEGDGE-crosslinked PVI under $N_2$, air and $O_2$.

FIGS. 12 and 13 show that the potential of the ceria nanoparticle electrode does not change between pH 4 (FIG. 12) and pH 8 (FIG. 13). FIG. 12 shows a cyclic voltammograms of a 3 mm vitreous carbon electrode coated with a film made of partially deoxygenated ceria nanoparticles, carbon and PEGDGE-crosslinked PVI under $N_2$ (solid line); air (dotted line) and $O_2$ (dashed line) (pH 4 citrate buffer; 5 mV/s scan rate) and FIG. 13 shows a cyclic voltammograms of a 3 mm vitreous carbon electrode coated with a film made of partially deoxygenated ceria nanoparticles, carbon and PEGDGE-crosslinked PVI under $N_2$ (solid line); air (dotted line) and $O_2$ (dashed line) (pH 8 imidazole-HCl buffer; 5 mV/s scan rate). At pH 4, a bound $O_2$-associated wave is upshifted by −120 mV to −80 mV versus Ag/AgCl (3M KCl), i.e. to −20 mV versus Ag/AgCl in physiological saline. In the pH 8 buffer the bound $O_2$-associated wave is downshifted by about −60 mV to −260 mV versus Ag/AgCl (3M KCl) i.e. to −190 mV versus Ag/AgCl in physiological saline. In the pH 4 solution, which was made with citrate buffer, a minor wave appeared at +0.49 V (AgCl).

Figure 14:
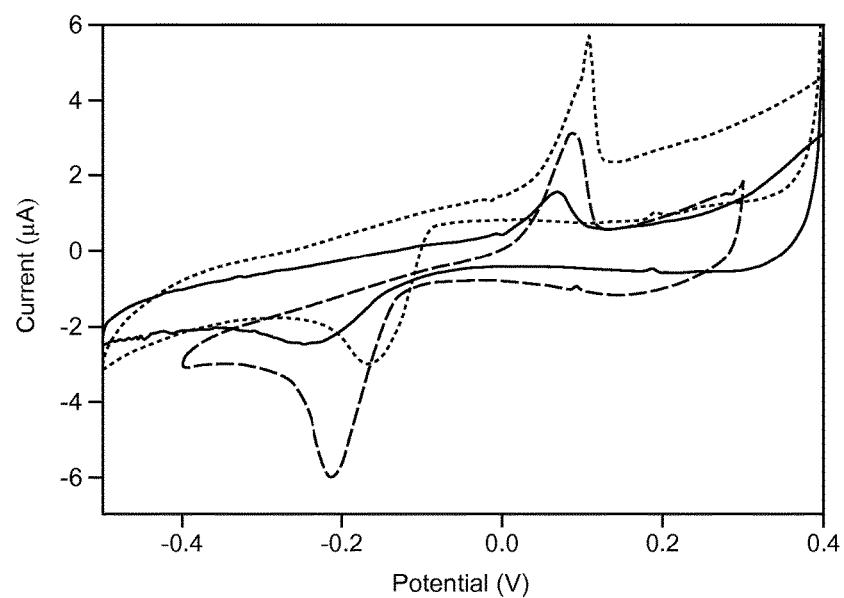
FIG. 14 shows a cyclic voltammograms of a vitreous carbon electrodes coated with ceria nanoparticles that were not deoxygenated and carbon, bound with PEGDGE-crosslinked PVI.

Chemisorption of phosphate onto the ceria nanoparticles slows the electrode reaction, causing separation of the anodic and cathodic waves by as much as 0.27 V at pH 6, 0.30 V at pH 7 and 0.30 V at pH 8. While phosphate chemisorption downshifts the half-cell potential by 0.07 V, it prevents the reactive binding of $O_2$. In the presence of 20 mM phosphate the half-cell potential does not change with pH (FIG. 14). FIG. 14 shows a cyclic voltammograms of a 3 mm diameter vitreous carbon electrodes coated with ceria nanoparticles that were not deoxygenated and carbon, bound with PEGDGE-crosslinked PVI (air atmosphere; 20 mM phosphate-0.1 M NaCl buffers of pH 6 (dotted line) (pH 7 (dashed line) and pH 9 (solid line); 1 mV/s scan rate).

Figure 15:
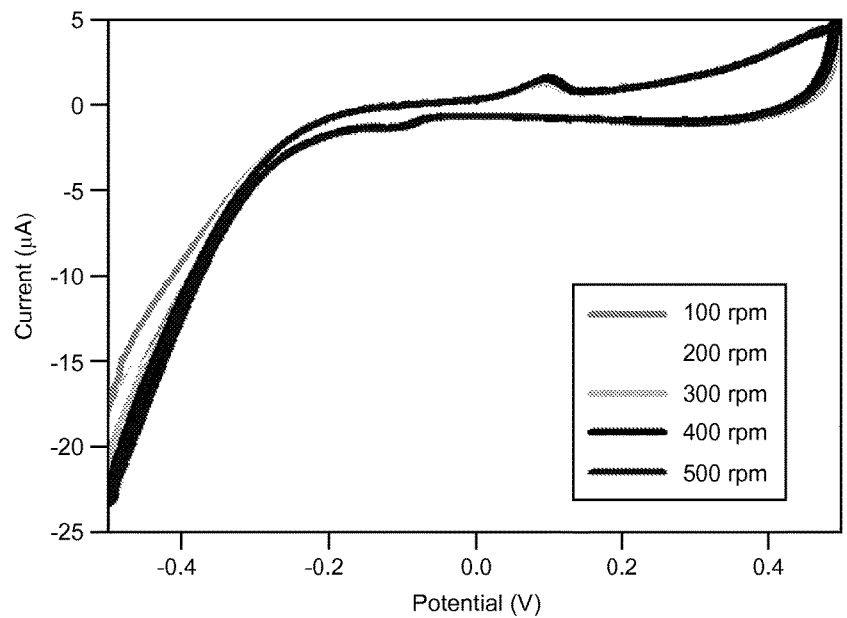
FIG. 15 shows the rotation-independence of the voltammetric waves near the Ag/AgCl electrode potential and rotation dependence of dissolved $O_2$ electroreduction.

When the ceria nanoparticle-carbon electrode, made with nanoparticles heated to 400° C. and with PEGDGE-crosslinked PVI was rotated in the 20 mM pH 7 phosphate buffer solution under air, the voltammetric wave near the potential of the Ag/AgCl electrode was independent of the angular velocity. The current was angular velocity, i.e. diffusional transport, dependent at potentials negative of −0.25 V vs. Ag/AgCl (3M KCl), the threshold for dissolved $O_2$ electroreduction (FIG. 15). FIG. 15 shows the rotation-independence of the voltammetric waves near the Ag/AgCl electrode potential and rotation dependence of dissolved $O_2$ electroreduction at potentials more reducing than −0.25 V versus Ag/AgCl (3 M KCl). 2 mm diameter vitreous carbon disk coated with ceria nanoparticle-carbon-PEGDGE-crosslinked PVI, air, pH 7 20 mM phosphate buffer, scan rate 5 mV/s.

Figure 16:
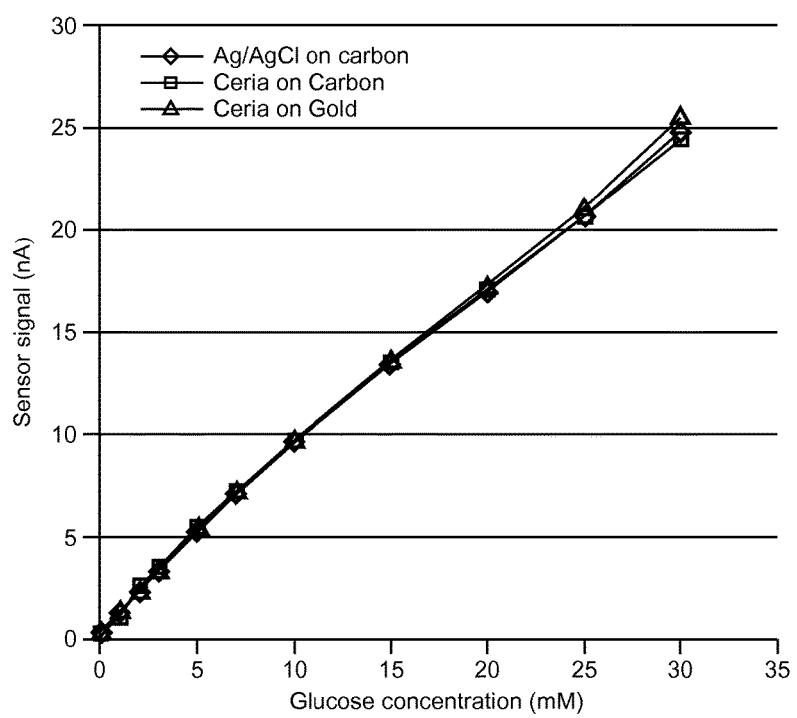
FIG. 16 shows the similarity of in-vitro calibration curves of amperometric glucose sensors made with Ag/AgCl reference, nanocrystalline $CeO_{2-x}$ on printed carbon and nanocrystalline $CeO_{2-x}$ on sputtered gold reference electrodes under air.
Figure 17:
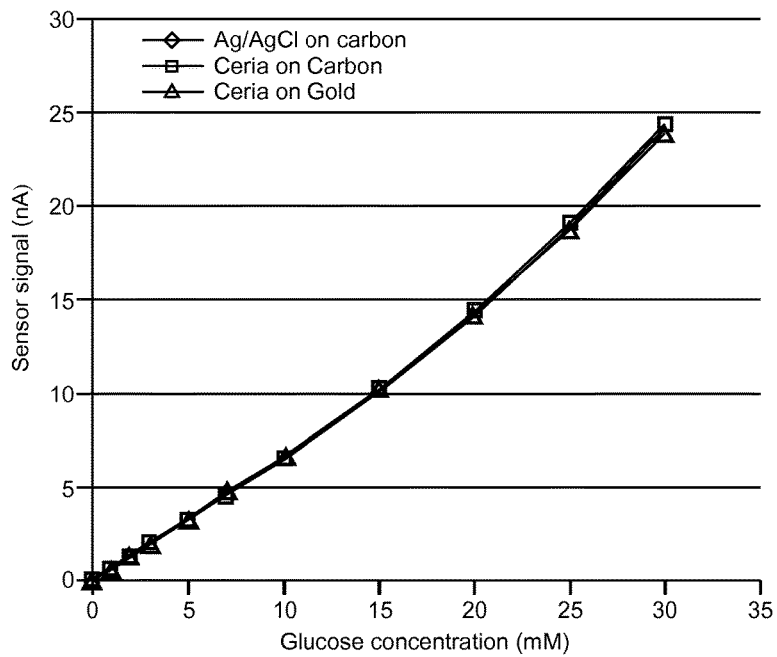
FIG. 17 shows the similarity of in-vitro calibration curves of amperometric glucose sensors made with Ag/AgCl reference, nanocrystalline $CeO_{2-x}$ on printed carbon and nanocrystalline $CeO_{2-x}$ on sputtered gold reference electrodes under 2% $O_2$.
Figure 18:
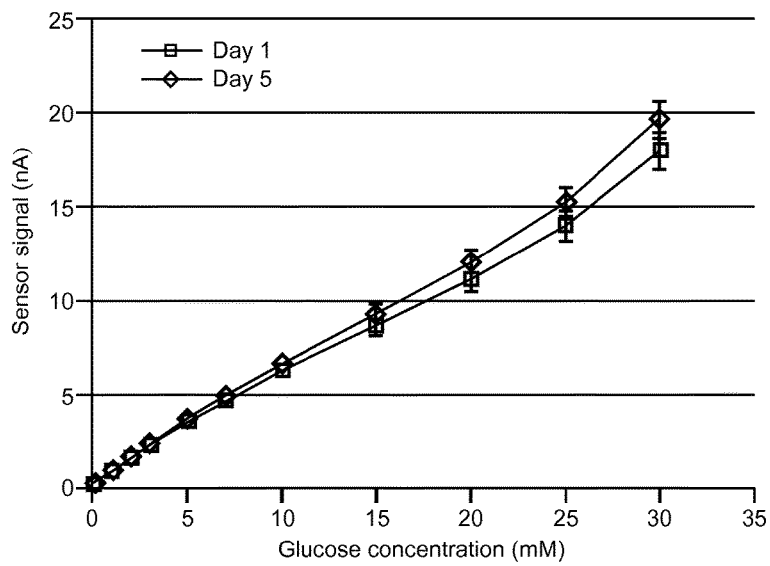
FIG. 18 shows sensitivities of amperometric glucose sensors made with ceria nanoparticle on printed carbon reference electrodes.

The in-vitro calibration curves of glucose sensors, designed for continuous operation upon their subcutaneous implantation (Feldman et al. Diabetes Technol. Ther. 2003, 5, 769), were indistinguishable when made with reference electrodes comprising Ag/AgCl on printed carbon, ceria embedded in PEGDGE-crosslinked PVI on printed carbon, or ceria embedded in PEGDGE-crosslinked PVI on sputtered gold. This was the case when the sensors operated in air (FIG. 16) and when they operated in 2% $O_2$ (balance: $N_2$) (FIG. 17). FIG. 16 shows the similarity of in-vitro calibration curves of amperometric glucose sensors made with Ag/AgCl reference (diamonds), nanocrystalline $CeO_{2-x}$ on printed carbon (squares) and nanocrystalline $CeO_{2-x}$ on sputtered gold (triangles) reference electrodes under air and FIG. 17 shows the similarity of in-vitro calibration curves of amperometric glucose sensors made with Ag/AgCl reference (diamonds), nanocrystalline $CeO_{2-x}$ on printed carbon (squares) and nanocrystalline $CeO_{2-x}$ on sputtered gold reference (triangles) electrodes under 2% $O_2$. Furthermore, the initial and the >$5^{th}$ day sensitivities of a set of 24 sensors made with ceria embedded in PEGDGE-crosslinked PVI on printed carbon reference electrodes changed by only ~10% after operating continuously at 37° C. in 17 mM glucose under ambient air for 5 days in pH 7 20 mM phosphate buffered physiological saline and their nearly linear response was preserved (FIG. 18, initial (squares) and >$5^{th}$ day (diamonds). The sensors operated continuously in 17 mM glucose, pH 7 20 mM phosphate, physiological saline solution at 37° C. under ambient air. The error bars represent the standard deviation for the tested set of 24 sensors.).

Example 3

Ceria-Carbon-PVP Electrodes, Ceria-Carbon-PVDF Electrodes

Preparation of Electrode Pastes

An electrode paste was made that included, on a dry weight basis, 26% $CeO_2$, 26% carbon black, 6% graphite, 37% poly-4-vinylpyridine (ca. 20,000 MW) and 6% polyethylene glycol (MW 400) diglycidyl ether.

The ceria-carbon mixture (referred to herein as "CeO2-C 0321B"), was prepared by combining 1.8 g carbon black, 0.4 g graphite, 7.4 mL ceria acetate colloid and 17.6 mL of 3% (v/v) acetic acid. The mixture had 4.0 g total solids (excluding acetate) in 25 mL total liquids or 16% solids. The material was milled in a Fritsch Pulverisette 6 ball mill. It was found that this method is more reproducible than hand mixing in a mortar and pestle. The material was placed upon 100 g of 3 mm zirconia balls in an 80 mL zirconia grinding bowl. The mill was run at 400 rpm ("medium mixing") for 60 minutes, total. (The 60 minutes of mixing were divided into six 10 minute runs with 3 minutes "rest" and reversal in between.) The ceria-carbon mixture was withdrawn by pipette from among the milling balls.

The P4VP-based electrode paste was prepared by combining 1.0 mL of CeO2-C 0321B, 5.2 mL of 2% (w/v) poly-4-vinylpyridiene (in 1.2% (v/v) acetic acid) and 0.16 mL of 1:10 diluted PEGDGE. The paste has 0.14 g total solids (excluding acetate) in 3.2 mL total liquids, or 4.4% solids. First, 1 mL of CeO2-C, 5.2 mL of P4VP binder and 30 g of zirconia balls were milled for 20 minutes (10 run+3 rest) at 400 rpm in the Pulverisette. It was found that this method produced a more homogeneous dispersion than vortex mixing, which can leave clumps which can cause cracking Second, 2.5 mL of the homogenized CeO2-C+ P4VP was combined with 0.080 mL of 1:10 diluted PEGDGE and vortexed for 20 seconds.

Immediately after vortexing, the paste was pipetted and spread on a printed carbon electrode. The aliquot was almost always 5 uL in a 6 mm by 3 mm area, or 28 uL/cm². The printed carbon electrode was a commercially available screen-printed carbon electrode, typically, the carbon half of a strip for blood glucose testing. The electrode was prepared by exposing it to air plasma, due to an imperfect vacuum, for approximately one minute in a Harrick plasma cleaner operating at its medium RF power setting. Plasma treatment made it easily wetted. Its unused area was masked with a thin coat of nail polish to leave an approximately 6 mm by 3 mm test area at the end.

For single-layer tests, the paste was dried-cured on the electrodes overnight at room temperature (about 25° C.), sometimes in a 75-80% humidity chamber and sometimes in ambient humidity, which varied from about 20% to 50%. For multi-layer tests, the paste was dried under an infrared lamp. The 250 watt lamp was about 9 inches above the electrodes, the illuminated area temperature was 40° C. to 47° C., and the humidity was ambient. Drying times were about 20 minutes for the first layers and decreased to about 10 minutes for the last layers. Drying was assessed visually.

Electrode pastes with PVDF were prepared the same way P4VP-based pastes were prepared, except that 0.5%, 1% or 2% (w/v) poly-vinylidenefluoride (in N-methylpyrrolidone (NMP)) was substituted for the P4VP solution.

Coulombic Capacity

The electrodes were tested for coulombic capacities by the amperometric i-t procedure. In a three electrode cell, the working electrode was the electrode described above, the reference was a Ag/AgCl (3M KCl) electrode and the counter electrode was a platinum coil or a graphite rod. The solution in the cell was pH 7.2 buffer made with 20 mM phosphate and 100 mM sodium chloride. The potentiostat was a CH Instruments Model 660A, and its control and data acquisition were by CH Instruments software. Tests were run at room temperature, approximately 23° C. Before a test, the electrode was immersed in buffer for 1 minute. During a test, the electrode was poised at −0.2 V vs. the reference, and the current (i) as a function of time (t) was measured. The i-t data was integrated to give total charge passed as a function of time. The total charge passed after 6, 20, 250 and 1000 s was the coulombic capacity at those times.

Table 1 shows the coulombic capacities of electrodes made from different batches of P4VP-based electrode paste. For one-layer electrodes, the mean coulombic capacities were −0.96 and −1.6 milli-coulombs/cm$^2$ in 6 and 20 seconds, respectively. For many one-layer electrodes, the current was approaching zero, and sometimes going slightly positive, before 250 seconds had elapsed. For five-layer electrodes, the mean coulombic capacities were −4.8, −13, −49 and −69 milli-coulombs/cm$^2$ in 6, 20, 250 and 1000 seconds, respectively.

The theoretical capacity of a one-layer electrode was 32 milli-coulombs, based on the calculation below. Scaled by area, it was 180 milli-coulombs/cm$^2$. The theoretical capacity of a five-layer electrode was 890 milli-coulombs/cm$^2$. For one-layer electrodes, the mean coulombic capacity in 20 seconds was about 1% of the theoretical capacity. For five-layer electrodes, the mean coulombic capacity in 20 and 1000 seconds was about 1.5% and 8% of theoretical capacity. In 48 hour tests of two 20-layer electrodes, the coulombic capacity was 720 milli-coulombs/cm$^2$, which was 20% of the theoretical capacity of a 20 layer electrode ([(5×10$^{-3}$ mL paste)×(4.4% solids in paste)×(26% CeO2 in solids)/(172 g/mol CeO$_2$)]×(96500 C/mol)).

For a group of one-layer electrodes made with polyvinylidene fluoride (PVDF) instead of P4VP electrode paste, the mean coulombic capacities were −1.8, −4.1 and −14 milli-coulombs/cm$^2$ in 6, 20 and 250 seconds, respectively. For another group of six-layer electrodes made with PVDF the mean coulombic capacities were −7.1, −19 and −74 milli-coulombs/cm$^2$ in 6, 20 and 250 seconds, respectively.

Batch Reproducibility and Shelf Life

For Batches #1 through #5, the relative standard deviation of the coulombic capacities was about 50%. Batch #5 raised the variability substantially, but there was no reason to exclude it from the dataset.

Ceria-Carbon pastes without the binder that were stored for 20 and 29 days before testing (Batches #1 and #2, respectively) had capacities that were similar to the capacities of fresh pastes.

Cracking and Peeling

FIG. 19 shows a series of micrographs of dried ceria-carbon paste coated on conventional printed carbon electrodes: single-layer (Panels A and B) and six-layer (Panels C and D). The original magnification was ~40× for Panels A and C; the Panels B and D are enlargements of Panels A and C. In four batches of single-layer electrodes (total 27) and two batches of double-layer electrodes (total 15), no electrodes had cracking visible to the naked eye or observed under 2× magnification (magnifying glass) or observed under >40× magnification (inspection microscope). In single batches of multi-layer electrodes (5 electrodes per batch), no cracks were seen until 10 layers were applied. At that point, "mud cracking" began, apparently the result of crude drying.

Single-layer electrodes were examined for material loss with the tape peel test. Neither a weak peel (with a post-it

TABLE 1

Coulombic capacity test strips made from different batches of P4VP-based electrode paste.

| Note | Batch | Batch Prep'd | Homogenized | Strips Prep'd | n | mcoul/cm$^2$ at 6 sec mean | stdev | n | mcoul/cm$^2$ at 20 sec mean | stdev | n | mcoul/cm$^2$ 250 sec mean | stdev | n | mcoul/cm$^2$ at 1000 sec mean | stdev |
|---|---|---|---|---|---|---|---|---|---|---|---|---|---|---|---|---|
| | | | | | | 1 layer | | | | | | | | | | |
| 1 | 2 | 4/26 | 5/24 | 5/24 | 6 | −1.19 | 0.18 | 6 | −2.03 | 0.40 | | | | | | |
| 0 | 3 | 5/22 | 5/24 | 5/24 | 7 | −0.81 | 0.22 | 7 | −1.32 | 0.46 | | | | | | |
| 0 | 4 | 5/27 | 5/27 | 5/27 | 5 | −0.83 | 0.23 | 5 | −1.37 | 0.39 | | | | | | |
| 0 | 5 | 5/30 | 5/30 | 5/30 | 5 | −1.01 | 0.18 | 4 | −1.70 | 0.27 | | | | | | |
| | Mean | | | | | −0.96 | | | −1.62 | | | | | | | |
| | Range % | of mean | | | | 40% | | | 47% | | | | | | | |
| | | | | | | 5 layers | | | | | | | | | | |
| 1 | 1 | 3/21 | n/a | 4/9 | 4 | −4.63 | 0.54 | 4 | −12.42 | 1.61 | 4 | −47.92 | 9.49 | 4 | −67.62 | 14.44 |
| 1 | 2 | 4/26 | 5/24 | 5/24 | 3 | −4.78 | 0.46 | 3 | −12.93 | 1.18 | 3 | −52.52 | 6.86 | 3 | −75.44 | 11.20 |
| 0 | 3 | 5/22 | 5/24 | 5/24 | 3 | −4.28 | 0.50 | 3 | −11.21 | 1.30 | 3 | −39.66 | 5.34 | 3 | −54.54 | 8.05 |
| 0 | 4 | 5/27 | 5/27 | 5/29 | 3 | −4.18 | 0.20 | 3 | −11.25 | 0.67 | 3 | −40.71 | 6.96 | 3 | −56.54 | 11.05 |
| 0 | 5 | 5/30 | 5/30 | 5/30 | 3 | −6.32 | 0.48 | 3 | −17.24 | 1.34 | 3 | −65.00 | 7.77 | 3 | −91.49 | 11.98 |
| | Mean | | | | | −4.84 | | | −13.01 | | | −49.16 | | | −69.13 | |
| | Range % | of mean | | | | 44% | | | 46% | | | 52% | | | 53% | |
| | | | | | | 5 layers | | | | | | | | | | |
| 2 | 2 | 4/26 | 5/24 | 5/29 | 3 | −5.25 | 0.50 | 3 | −12.04 | 1.47 | 3 | −27.78 | 4.506 | 3 | −35.80 | 4.94 |
| 2 | 3 | 5/22 | 5/24 | 5/29 | 3 | −4.15 | 0.62 | 3 | −8.78 | 1.56 | 3 | −19.05 | 3.99 | 3 | −26.80 | 6.26 |
| 2 | 4 | 5/27 | 5/27 | 5/29 | 3 | −4.28 | 0.46 | 3 | −9.84 | 1.13 | 3 | −24.17 | 2.84 | 3 | −32.15 | 4.73 | note) nor a moderate peel (with scotch magic tape) removed material visible to the naked eye.

Coulombic Capacity vs. Layers

Figure 20:
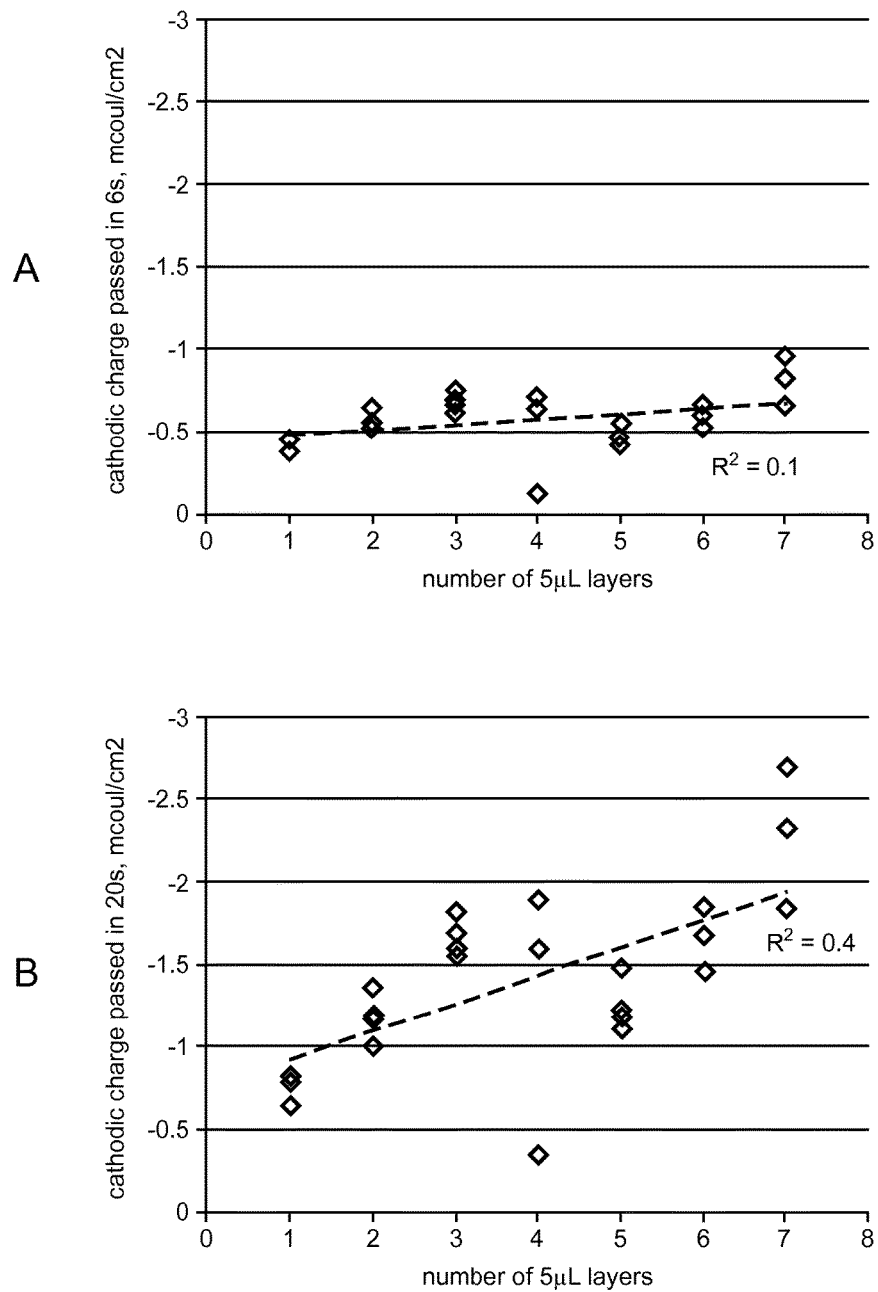
FIGS. 20A-D shows graphs of cathodic charge passed vs. number of layers for ceria electrodes.
Figure 20:
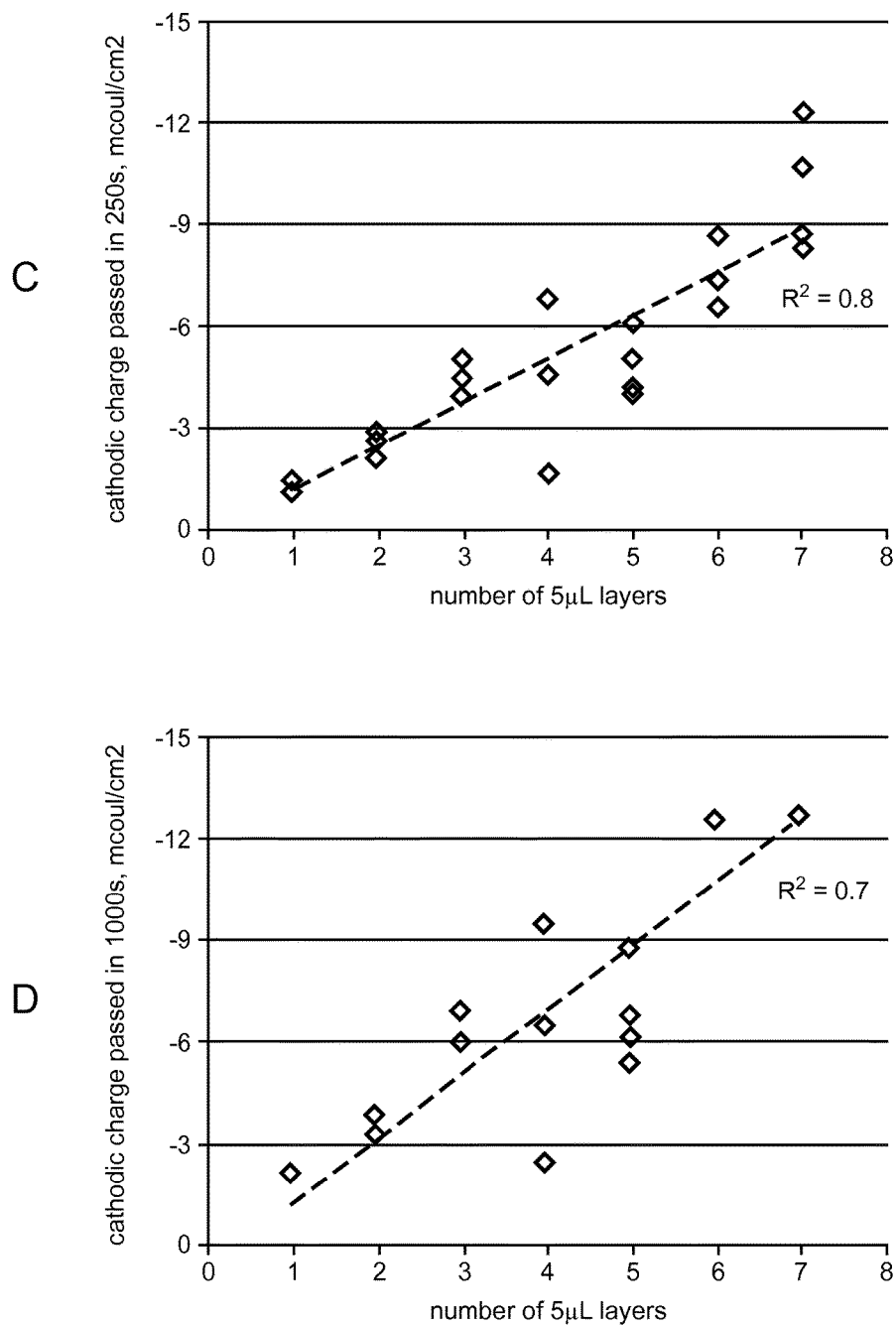

FIG. 20 shows graphs of coulombic capacity of the electrodes as a function of the number of applied layers. While multiple layers had little effect on coulombic capacity at short times (6 s), they had more effect as time increased. From 1 to 7 layers, the capacity increased by a factor of 3 at 20 s, and by a factor of 8-9 at 250 s and 1000 s. The four graphs show charge passed in 6 s (Panel A), 20 s (Panel B), 250 s (Panel C), and 1000 s (Panel D). The vertical axis is cathodic charge passed and it is 0 to −3 milli-coulombs/cm$^2$ for Panels A and B and 0 to −15 milli-coulombs/cm$^2$ for Panels C and D. The horizontal axis is number of 5 uL layers, and it is 0 to 7 for all graphs.

The present description should not be considered limited to the particular examples described above, but rather should be understood to cover all aspects as will be readily apparent to those of skill in the art upon review of the instant specification.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An electrode assembly for an in vivo electrochemical sensor, the electrode assembly comprising:
   a first electrode comprising an analyte responsive enzyme; and
   a second electrode in electrical communication with the first electrode, the second electrode comprising a substrate and a ceria nanoparticle composition applied upon the substrate, the ceria nanoparticle composition having a total mass of ceria nanoparticles per cm$^2$ of substrate area in a range of 0.1 mg/cm$^2$ to 100 mg/cm$^2$.

2. The electrode assembly according to claim 1, wherein the ceria nanoparticles have the formula $CeO_{2-x}$ and x ranges from 0 to 0.5.

3. The electrode assembly according to claim 2, wherein x ranges from 0.01 to 0.2 for 50% or greater of the ceria nanoparticles.

4. The electrode assembly according to claim 1, wherein at least a portion of the ceria nanoparticles comprise oxygen anion vacancy defects.

5. The electrode assembly according to claim 1, wherein the ceria nanoparticles have a particle size range of from 1 nm to 100 nm.

6. The electrode assembly according to claim 1, wherein the ceria nanoparticle composition further comprises a conductive material comprising branched carbon black particles having a diameter of 2 nm to 50 nm.

7. The electrode assembly according to claim 1,
   wherein the substrate is conductive, or
   wherein the substrate is non-conductive and is coated with a conductive material, the ceria nanoparticle composition being applied upon the conductive material.

8. The electrode assembly according to claim 1, wherein the ceria nanoparticle composition further comprises a polymer, the polymer being water soluble or water swellable.

9. The electrode assembly according to claim 8, wherein the polymer is a nitrogen containing polymer.

10. The electrode assembly according to claim 1, wherein the ceria nanoparticle composition comprises a weight percentage of ceria nanoparticles from 10% to 80%.

11. The electrode assembly according to claim 7, wherein the conductive material comprises a conductive polymer.

12. The electrode assembly according to claim 2, wherein x ranges from 0.2 to 0.5 for 50% or greater of the ceria nanoparticles.

13. The electrode assembly according to claim 1, wherein the ceria nanoparticles have the formula $Ce_2O_3$.

14. The electrode assembly according to claim 4, wherein 1% to 20% of oxygen sites on the portion of the ceria nanoparticles are oxygen anion vacancy defects.

15. The electrode assembly according to claim 1, wherein at least a portion of the ceria nanoparticles are doped with a dopant selected from the group consisting of lanthanum, copper, zinc, cobalt, calcium, aluminum, and any combination thereof, the dopant being present in a range of 1 mole percent to 25 mole percent.

16. The electrode assembly according to claim 1, wherein the total mass of ceria nanoparticles per cm$^2$ of substrate area is in the range of 0.1 mg/cm$^2$ to 9 mg/cm$^2$.

17. The electrode assembly according to claim 1, wherein the ceria nanoparticle composition further comprises an inorganic acid or an organic acid.

18. The electrode assembly according to claim 1, wherein the ceria nanoparticle composition further comprises an organic acid in the range of 0.01 w/v % to 1 w/v %.

19. The electrode assembly according to claim 1, wherein the ceria nanoparticle composition further comprises a binder in the range of 1% by weight to 25% by weight.

20. The electrode assembly according to claim 1, wherein the ceria nanoparticle composition further comprises a cationic surfactant in the range of 0.1% by weight to 1% by weight.

21. The electrode assembly according to claim 1, wherein the ceria nanoparticle composition further comprises an organic polymer and a weight ratio of ceria nanoparticles to organic polymer ranging from 1:1 to 1:10.

22. The electrode assembly according to claim 1, wherein the first electrode is an anode, and the second electrode is a cathode or a reference electrode.

23. The electrode assembly according to claim 1, wherein the substrate has a length in a range of 0.1 mm to 5.0 mm, and a width in a range of 0.1 mm to 5.0 mm.

24. The electrode assembly according to claim 1, wherein the ceria nanoparticle composition comprises one or more layers and has a total thickness in a range of 0.1 μm to 100 μm.

25. The electrode assembly according to claim 1, wherein the ceria nanoparticle composition further comprises a zwitterionic polymer.

* * * * *